(12) United States Patent
Li et al.

(10) Patent No.: US 6,639,064 B1
(45) Date of Patent: Oct. 28, 2003

(54) NRIF3, NOVEL CO-ACTIVATOR FOR NUCLEAR HORMONE RECEPTORS

(75) Inventors: Dangsheng Li, New York, NY (US); Vandana Yajnik, Brookline, MA (US); Herbert H. Samuels, New Rochelle, NY (US)

(73) Assignee: New York University, New York, NY (US)

( * ) Notice: Subject to any disclaimer, the term of this patent is extended or adjusted under 35 U.S.C. 154(b) by 12 days.

(21) Appl. No.: 09/662,052

(22) Filed: Sep. 15, 2000

(65) Prior Publication Data (65)

Related U.S. Application Data
(60) Provisional application No. 60/154,347, filed on Sep. 17, 1999.

(51) Int. Cl.[7] .................. C07H 21/04; C12P 21/04; C12N 1/14; C12N 1/16; C12N 1/18
(52) U.S. Cl. ............. 536/23.5; 435/71.1; 435/254.1; 435/254.2; 435/255.1; 435/320.1; 435/325; 536/23.1
(58) Field of Search ................. 435/6, 7.31, 91.1, 435/320.1, 325, 254.1, 254.2, 255.1, 71.1; 536/23.1, 24.3, 23.5

(56) References Cited

FOREIGN PATENT DOCUMENTS

WO    WO 98/18927    *   5/1998   ............. 435/7.31

OTHER PUBLICATIONS

Sequence Search—Result 29—for WO 98/18927, 1998.*
Anzick et al., Science, 277:965–968, Aug. 15, 1997.
Baniahmad et al., Molecular and Cellular Biology, 15:76–86, Jan. 1995.
Barettino et al., The EMBO Journal, 13(13):3039–3049, 1994.
Chakravarti et al., Nature, 383:99–103, Sep. 5, 1996.
Chen et al., Cell, 90:569–580, Aug. 8, 1997.
Darimont et al., Genes & Development, 12:3343–3356, 1998.
Durand et al., The EMBO Journal, 13(22):5370–5382, 1994.
Feng et al., Science, 280:1747–1749, Jun. 12, 1998.
Forman et al., Molecular Endocrinolgy, 6(3):429–442.
Glass et al, Cell Biology, 9:222–232, 1997.
Hanstein et al., Proc. Natl. Acad. Sci. USA, 93:11540–11545, Oct. 1996.
Heery et al., Nature, 387:733–736, Jun. 12, 1997.
Hong et al., Proc. Natl. Acad. Sci. USA, 93:4948–4952, May 1996.
Hong et al., Molecular and Cellular Biology, 2735–2744, May 1997.
Kamei et al., Cell, 85:403–414, May 3, 1996.
Lanz et al., Cell, 97:17–27, Apr. 2, 1999.
Leng et al., Molecular and Cellular Biology, 15(1):255–263, Jan. 1995.
Li et al., Proc. Natl. Acad. Sci. USA, 94:8479–8484, Aug. 1997.
Mangelsdorf et al., Cell, 83:841–850, Dec. 15, 1995.
Mangelsdorf et al., Cell, 83:835–839, Dec. 15, 1995.
McInerney et al., Genes and Development, 12:3357–3368, 1998.
Nolte et al., Nature, 395:137–143, Sep. 10, 1998.
Oñate et al., Science, 270:1354–1357, Nov. 24, 1995.
Piugserver et al., Cell, 92:829–839, Mar. 20, 1998.
Takeshita et al., J. Biological Chemistry, 272(44):27629–27634, Oct. 31, 1997.
Torchia et al., Nature, 387:677–684, Jun. 1997.
Umesono et al., Cell, 57:1139–1146, Jun. 30, 1989.
Umesono et al., Cell, 65:1255–1266, Jun. 28, 1991.
Voegel et al, The EMBO Journal, 15(14):3667–3675, 1996.
Yeh et al., Proc. Natl. Acad. Sci. USA, 93:5517–5521, May 1996.

* cited by examiner

*Primary Examiner*—Jehanne Souaya
(74) *Attorney, Agent, or Firm*—Darby & Darby

(57) ABSTRACT

Nucleic acids encoding NRIF3 are described. Polypeptides having amino acid sequences of NRIF3 proteins are also provided. A method is also provided for isolating and cloning NRIF3 cDNA. NRIF3 is useful in development/implementation of high throughput screens to identify novel thyroid hormone receptor (TR) and retinoid X receptor (RXR) agonists and antagonists. Methods are also provided for identifying compounds that directly interfere with the interaction of NRIF3 and TR or RXR. Finally, therapies based on modulation of NRIF3 activity are disclosed.

9 Claims, 15 Drawing Sheets

```
  1 CAGCGGGCAGTGGTGCTTTCCCCAATCTCAGAATGCCTGTTAAAGATCACTGAAGTTGGA
                    M  P  V  K  R  S  L  K  L  D   10

61 TGGTCTCTGTTAGAAGAAAATTCATTTGATCCTTCAAAAATCACAAGGAAGAAAGTGTTAT
     G  L  L  E  E  N  S  F  D  P  S  K  I  T  R  K  K  S  V  I   30

121 AACTTATTCTCCAACAACTGGAACTTGTCAAATGAGTCTATTTGCTTCTCCCACAAGTTC
     T  Y  S  P  T  T  G  T  C  Q  M  S  L  F  A  S  P  T  S  S   50

181 TGAAGAGCAAAAGCACAGAAATGGACTATCAAATGAAAAGAGAAAAAAATTGAATCACCC
     E  E  Q  K  H  R  N  G  L  S  N  E  K  R  K  K  L  N  H  P   70

241 CAGTTTAACTGAAAGCAAAGAATCTACAACAAAAGACAATGATGAATTCATGATGTTGCT
     S  L  T  E  S  K  E  S  T  T  K  D  N  D  E  F  M  M  L  L   90

301 ATCAAAAGTTGAGAAATTGTCAGAAGAAATCATGGAGATAATGCAAAATTTAAGTAGTAT
     S  K  V  E  K  L  S  E  E  I  M  E  I  M  Q  N  L  S  S  I   110

361 ACAGGCTTTGGAGGGCAGTAGAGAGCTTGAAAATCTCATTGGAATCTCCTGTGCATCACA
     Q  A  L  E  G  S  R  E  L  E  N  L  I  G  I  S  C  A  S  H   130

421 TTTCTTAAAAAGAGAAATGCAGAAAACCAAAGAACTAATGACAAAAGTGAATAAACAAAA
     F  L  K  R  E  M  Q  K  T  K  E  L  M  T  K  V  N  K  Q  K   150

481 ACTGTTTGAAAAGAGTACAGGACTTCCTCACAAAGCATCACGTCATCTTGACAGCTATGA
     L  F  E  K  S  T  G  L  P  H  K  A  S  R  H  L  D  S  Y  E   170

541 ATTCCTTAAAGCCATTTTAAACTGAGGCATTAAGAAGAAATGCACTCACCATGAGCACCA
     F  L  K  A  I  L  N  *
```

Figure 2

GFP

GFP-NRIF3

NRIF3, NOVEL CO-ACTIVATOR FOR NUCLEAR HORMONE RECEPTORS

PRIORITY

This application claims priority under 35 U.S.C. §119 from provisional patent application Serial No. 60/154,347, filed Sep. 17, 1999, which is hereby incorporated by reference in its entirety.

The research leading to the present invention was supported, in part, by National Institutes of Health Grants No. DK09581 and No. DK16636-27. Accordingly, the United States Government has certain rights in the invention.

FIELD OF THE INVENTION

This invention relates to a novel nuclear hormone receptor co-activator. The invention further relates to high throughput screening assays with these receptors, as well as utilization of the co-activator for developing therapeutic measures for human diseases.

BACKGROUND OF THE INVENTION

Nuclear hormone receptors are ligand-regulated transcription factors that play diverse roles in cell growth, differentiation, development, and homeostasis. The nuclear receptor superfamily has been divided into two sub-families: the steroid receptor family and the thyroid hormone/retinoid (non-steroid) receptor family (51). The steroid receptor family includes receptors for glucocorticoids (GR), mineralcorticoids (MR), progestins (PR), androgens (AR) and estrogens (ERs) (51). The non-steroid receptor family includes receptors for thyroid hormones (TRs), retinoids (RARs and RXRs), 1,25-(OH)$_2$ vitamin D (VDR), prostanoids (PPARs) as well as many orphan receptors whose ligands (if any) remain to be defined (49, 51). Members of the nuclear receptor superfamily share common structural and functional motifs. Nevertheless, an important difference exists between the two sub-families. Steroid receptors primarily act as homodimers by binding to their cognate palindromic hormone response elements (HREs) (77, 78). In contrast, members of the non-steroid receptor family can bind to DNA as monomers, homodimers, and heterodimers (25, 78). Their corresponding HREs are also complex, and can be organized as direct repeats, inverted repeats, and everted repeats (49). Therefore, the combination of heterodimerization and HRE complexity provides the potential to generate enormous diversity in receptor-mediated regulation of target gene expression.

Structural and functional studies indicate that the ligand binding domain (LBD) of many members of the thyroid hormone/retinoid receptor family harbors diverse functions. In addition to ligand binding, the LBD also plays roles in mediating receptor dimerization, hormone-dependent transactivation, and in the case of TR and RAR, ligand-relieved gene silencing (54, 61). The carboxyl-terminal helix of the LBD has been implicated in playing an important role in ligand-dependent conformational changes and transactivation (6, 9, 21, 43). Although it has been suggested that an activation function (AF-2) resides in this C-terminal helix, recent studies indicate that AF-2 results from a ligand-induced conformational change involving diverse areas of the LBD (23, 66). Thus, ligand binding serves to switch the receptor from one functional state (e.g. inactive or silencing) to another (e.g. transactivation).

Although much has been learned from studying the structure and function of these receptors, the detailed molecular mechanism(s) of transcriptional regulation by these receptors is not well understood. Efforts to understand the molecular mechanism of transcriptional repression by unliganded TRs and RARs have led to the description (12) and isolation of putative co-repressor proteins SMRT and N-CoR, which interact with the LBD of these receptors in the absence of their ligands (15, 36). The recent discovery that both SMRT and N-CoR form complexes with Sin3 and a histone deacetylase suggests that chromatin remodeling by histone deacetylation may play a role in receptor-mediated transcriptional repression (33, 55).

In a somewhat parallel approach, the identification of co-activators has recently received extensive experimental attention in order to elucidate the molecular mechanism(s) of transcriptional activation by nuclear receptors (27). Identified co-activator proteins primarily belong to two groups: the SRC-1 family and the CBP/p300 family. The SRC-1 family includes SRC-1/NCoA-1 (37, 58, 74), and the related proteins GRIP1/TIF2/NCoA-2 (34, 35, 74, 79), and AIB1/p/CIP/ACTR/RAC3/TRAM-1 (2, 14, 44, 73, 74). The second group of co-activators includes CBP and its homolog p300, which not only influence the activity of nuclear receptors (13, 31, 37), but also functionally interact with many transcription factors such as CREB (3, 16, 40, 46), the Stats (10, 87), AP1 (4, 7), and p53 (28, 45). There are also co-activator proteins that do not belong to these two groups, such as ARA70 (85), PGC-1 (60), and the recently-reported RNA co-activator SRA (41). Members of both the SRC-1 family and CBP/p300 family have been shown to possess histone acetyltransferase (HAT) activities (8, 14, 57, 69), suggesting that chromatin remodeling by histone acetylation is an important mechanism involved in transcriptional activation by ligand-bound nuclear receptors.

Interaction of members of the SRC-1 and CBP/p300 families with nuclear receptors occurs through conserved LxxLL (SEQ ID NO:1) motifs (32), which interact with a hydrophobic cleft in the receptor LBD formed as a result of conformational changes mediated by ligand binding (19, 23, 56). In the sequence, x refers to any amino acid. SRC-1/NCoA-1 and GRIP1/TIF2 contain three LxxLL regions or boxes (referred to as LXDs or NR boxes) that differentially interact with nuclear receptors so that different nuclear receptors functionally utilize different LxxLL boxes (19, 52). Thus, ER utilizes the second LxxLL box of SRC-1/NCoA-1 while PR utilizes both the first and second LxxLL boxes for optimal interaction. In contrast, TR and RAR require both the second and third LxxLL boxes for optimal interaction (52). The specificity of receptor recognition by the different LxxLL boxes of SRC-1/NCoA-1 is primarily mediated by eight amino acid residues C-terminal to the LxxLL motif rather than by the two amino acids (xx) within the motif itself. Thus, while members of the SRC-1 family are capable of interacting with many nuclear receptors, the molecular detail of such interactions differs for each receptor in the number or combination of LxxLL boxes utilized as well as in the critical amino acid residues surrounding the LxxLL motifs.

While much has been learned from the study of known co-activators, a number of key mechanistic questions remain to be answered. For example, many nuclear receptors can recognize common DNA elements, (25, 49, 51), while not all are capable of regulating genes containing those elements (20, 47, 65). Thus, how native target genes containing such elements are selectively regulated by specific receptors is a very important but poorly-understood problem. Although the various LxxLL boxes of SRC-1 and GRIP1 show differential receptor preference (19, 52), these co-activators are unlikely to play a primary role in mediating effects that are receptor specific since they appear to interact with all ligand-bound nuclear hormone receptors. Thus, the detailed molecular mechanism(s) underlying receptor-specific regulation of gene expression remains to be elucidated. Whether co-activator(s) might contribute to this specificity is currently unknown.

SUMMARY OF THE INVENTION

The present invention discloses an isolated nucleic acid molecule comprising a sequence that encodes a functional NRIF3 nuclear hormone receptor co-activator, where the NRIF3 binds in a ligand dependent manner to thyroid hormone receptor (TR) and retinoid X receptor (RXR), but does not interact with retinoic acid receptor (RAR), vitamin D receptor (VDR), progesterone receptor (PR), glucocorticoid receptor (GR), and estrogen receptor (ER) in a yeast two hybrid assay system or in vitro, or both, and where the nucleic acid encodes a polypeptide that contains an LxxIL (SEQ ID NO:2) module in its C-terminal domain.

A hybridizable nucleic acid, of at least twenty bases, which has a sequence as depicted in SEQ ID NO:3 (FIG. 2) also is contemplated by the present invention.

The present invention also contemplates an isolated functional NRIF3 nuclear hormone receptor co-activator, where the NRIF3 binds in a ligand dependent manner to thyroid hormone receptor (TR) and retinoid X receptor (RXR), but does not interact with retinoic acid receptor (RAR), vitamin D receptor (VDR), progesterone receptor (PR), glucocorticoid receptor (GR), and estrogen receptor (ER) in a yeast two hybrid assay system or in vitro, or both, where the polypeptide contains an LxxIL (SEQ ID NO:2) module in its C-terminal domain.

A method for identifying a compound that modulates NFIR3 interaction with a nuclear hormone receptor is also contemplated by the present invention. The method comprises detecting modulation of the interaction of NFIR3 and TR or RXR in the presence of the compound.

BRIEF DESCRIPTION OF THE DRAWINGS

FIG. 2. Nucleotide (SEQ ID NO:3) and deduced amino acid (SEQ ID NO: 4) sequences of NRIF3. Only part of the cDNA sequence is shown. A putative nuclear localization signal (KRKK; SEQ ID NO:5) is underlined. The putative LxxLL (SEQ ID NO:1) motif is shown with a double underline. NRIF3 and the β3-endonexin long form (EnL) share 95% identity. They differ only in the C-terminus where the last 16 amino acids (dot underlined) in NRIF3 is replaced with 9 different amino acids (GQPQMSQPL; SEQ ID NO:6) in the β3-endonexin long form. The short form of β3-endonexin consists of 111 amino acids and is 100% identical to the first 111 amino acids of NRIF3 or the β3-endonexin long form.

DETAILED DESCRIPTION OF THE INVENTION

Figure 1:
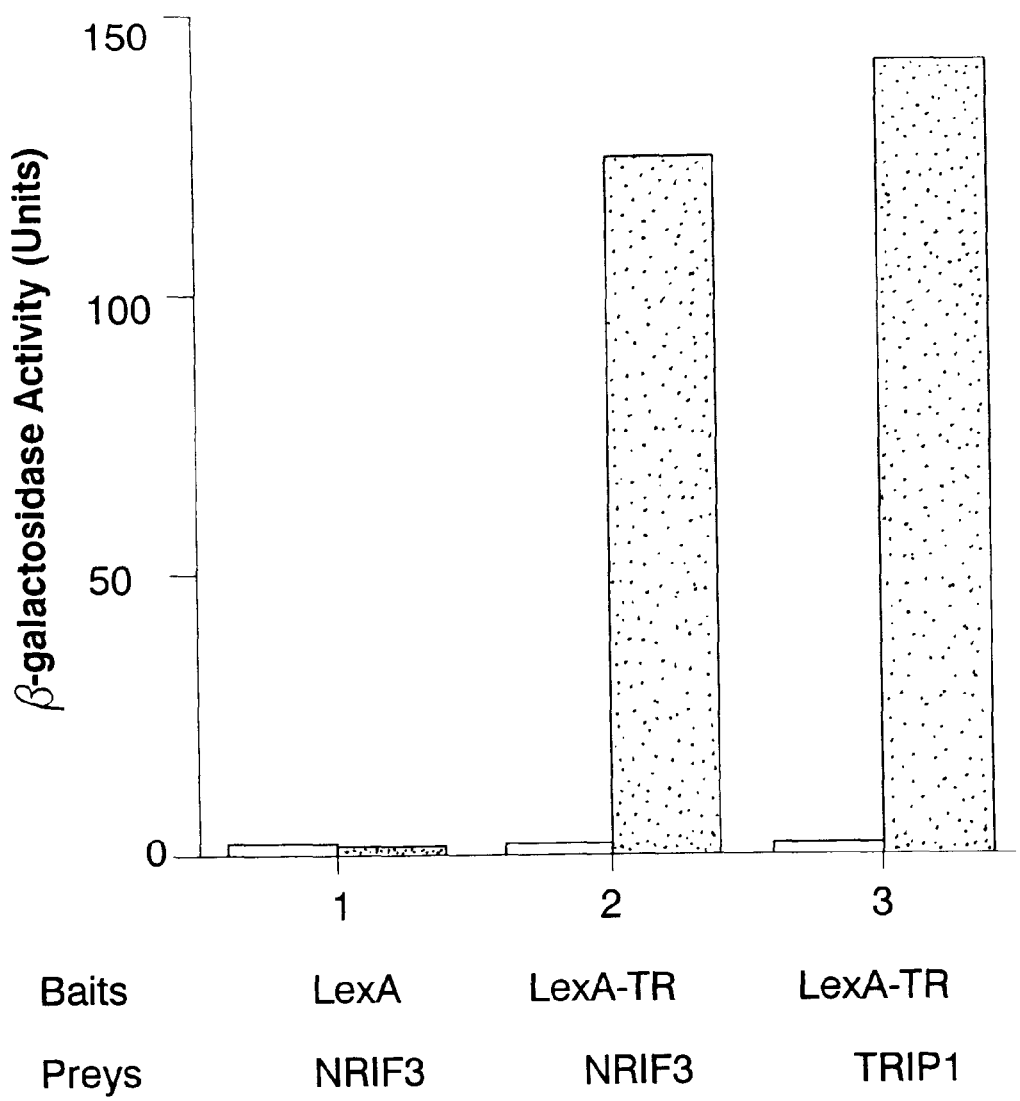
FIG. 1. Hormone-dependent interaction of NRIF3 with the ligand binding domain (LBD) of TR. Induction of β-galactosidase activity by thyroid hormone (T3) was measured in the yeast strain EGY48 transformed with a bait vector expressing LexA-cTRα LBD and the prey plasmid expressing NRIF3 fused to the B42 activation domain (29). The bait LexA alone was used as the negative control. The prey B42-Trip1 was used as the positive control.

Many nuclear receptors are capable of recognizing similar DNA elements. The molecular event(s) underlying the functional specificity of these receptors (in regulating the expression of their native target genes) is a very important question that remains poorly understood. The present invention is based, in part, on the cloning and analysis of a novel nuclear receptor co-activator (designated as NRIF3) that exhibits a distinct receptor specificity. Fluorescence microscopy shows that NRIF3 localizes to the cell nucleus. Yeast two-hybrid and/or in vitro binding assays indicate that NRIF3 specifically interacts with TR (thyroid hormone receptor) and RXR (retinoid X receptor) in a ligand-dependent fashion, but does not bind to RAR (retinoic acid receptor), VDR (vitamin D receptor), PR (progesterone receptor), GR (glucocorticoid receptor), or ER (estrogen receptor). Functional studies show that NRIF3 significantly potentiates TR- and RXR-mediated transactivation in vivo while little effect is observed for other examined nuclear receptors. Domain and mutagenesis analyses indicate that a novel C-terminal domain in NRIF3 plays an essential role in its specific interaction with liganded TR and RXR, while the N-terminal LxxLL (SEQ ID NO:1) motif plays a minor role in allowing optimum interaction. Computer modeling and subsequent experimental analysis suggest that the C-terminal domain of NRIF3 directly mediates interaction with liganded receptors through an LxxIL (SEQ ID NO:2)(a variant of the canonical LxxLL; SEQ ID NO:1) module, while other part of the NRIF3 protein may still play a role in conferring its receptor specificity. In the sequence, x refers to any amino acid. Identification of a co-activator with such a unique receptor specificity may provide new insight into the molecular mechanism(s) of receptor-mediated transcriptional activation as well as the functional specificity of nuclear receptors.

The use of italics indicates a nucleic acid molecule (e.g., NRIF3, cDNA, gene, etc.); normal text indicates the polypeptide or protein.

Genes Encoding NRIF3 Proteins

The present invention provides a gene encoding a NRIF3 of the invention, including a full length, or naturally occurring form of NRIF3, genomic NRIF3, splice variants of NRIF3 and any antigenic fragments thereof from any human source.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a recombinant nucleic acid construct, such as plasmid, phage genome, virus genome, cosmid, or artificial chromosome, to which another DNA segment may be attached. In a specific embodiment, the vector may bring about the replication of the attached segment, e.g., in the case of a cloning vector. A "replicon" is any genetic element (e.g., plasmid, chromosome, virus) that functions as an autonomous unit of DNA replication in vivo, i.e., it is capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA is expressed and effects a function or phenotype on the cell in which it is expressed.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A "polynucleotide" or "nucleotide sequence" is a series of nucleotide bases (also called "nucleotides") in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The polynucleotides.herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. Host cells can further be used for screening or other assays, as described infra.

Proteins and enzymes are made in the host cell using instructions in DNA and RNA, according to the genetic code. Generally, a DNA sequence having instructions for a particular protein or enzyme is "transcribed" into a corresponding sequence of RNA. The RNA sequence in turn is "translated" into the sequence of amino acids which form the protein or enzyme. An "amino acid sequence" is any chain of two or more amino acids. Each amino acid is represented in DNA or RNA by one or more triplets of nucleotides. Each triplet forms a codon, corresponding to an amino acid. For example, the amino acid lysine (Lys) can be coded by the nucleotide triplet or codon AAA or by the codon AAG. (The genetic code has some redundancy, also called degeneracy, meaning that most amino acids have more than one corresponding codon.) Because the nucleotides in DNA and RNA sequences are read in groups of three for protein production, it is important to begin reading the sequence at the correct amino acid, so that the correct triplets are read. The way that a nucleotide sequence is grouped into codons is called the "reading frame."

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as regions (consensus sequences) responsible for the binding of RNA polymerase machinery.

A coding sequence is "under the control of" or "operatively associated with" transcriptional and translational control sequences in a cell when RNA polymerase transcribes the coding sequence into mRNA, which is then trans-RNA spliced (if it contains introns) and translated into the protein encoded by the coding sequence.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include plasmids, phages, viruses, etc.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes.

The term "expression system" means a host cell and compatible vector under suitable conditions, e.g. for the expression of a protein coded for by foreign DNA carried by the vector and introduced to the host cell. Common expression systems include E. coli host cells and plasmid vectors, and insect host cells and Baculovirus vectors.

The term "heterologous" refers to a combination of elements not naturally occurring together. For example, heterologous DNA refers to DNA not naturally located in the cell, or in a chromosomal site of the cell. Preferably, the heterologous DNA includes a gene foreign to the cell. A heterologous expression regulatory element is a such an element operatively associated with a different gene than the one it is operatively associated with in nature. In the context of the present invention, an NRIF3 gene is heterologous to the vector DNA in which it is inserted for cloning or expression, and it is heterologous to a host cell containing such a vector, in which it is expressed, e.g., a CHO cell.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. The term "variant" may also be used to indicate a modified or altered gene, DNA sequence, enzyme, cell, etc., i.e., any kind of mutant.

"Sequence-conservative variants" of a polynucleotide sequence are those in which a change of one or more nucleotides in a given codon position results in no alteration in the amino acid encoded at that position.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck el al., Cell 50:667, 1987). Such proteins (and their encoding genes) have sequence homology, as reflected by their sequence similarity, whether in terms of percent similarity or the presence of specific residues or motifs.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 80%, and most preferably at least about 90 or 95%) of the nucleotides match over the defined length of the DNA sequences, as determined by sequence comparison algorithms, such as BLAST, FASTA, DNA Strider, etc. An example of such a sequence is an allelic or species variant of the specific NRIF3 genes of the invention. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80% of the amino acids are identical, or greater than about 90% are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs described above (BLAST, FASTA, etc.).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

Another gene encoding NRIF3 (in addition to the full length cDNA disclosed herein), whether genomic DNA or cDNA (such as splice variants), can be isolated from any source, particularly from a human cDNA or genomic library. Methods for obtaining NRIF3 gene are well known in the art, as described above (see, e.g., Sambrook et al., 1989, supra). The DNA may be obtained by standard procedures known in the art from cloned DNA (e.g., a DNA "library"), and preferably is obtained from a cDNA library prepared from tissues with high level expression of the protein, by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene. Identification of the specific DNA fragment containing the desired NRIF3 gene may be accomplished in a number of ways. For example, a portion of a NRIF3 gene exemplified infra can be purified and labeled to prepare a labeled probe, and the generated DNA may be screened by nucleic acid hybridization to the labeled probe (Benton and Davis, Science 196:180, 1977; Grunstein and Hogness, Proc. Natl. Acad. Sci. U.S.A. 72:3961, 1975). Those DNA fragments with substantial homology to the probe, such as an allelic variant from another individual, will hybridize. In a specific embodiment, highest stringency hybridization conditions are used to identify a homologous NRIF3 gene.

Further selection can be carried out on the basis of the properties of the gene, e.g., if the gene encodes a protein product having the isoelectric, electrophoretic, amino acid composition, partial or complete amino acid sequence, antibody binding activity, or receptor binding profile of NRIF3 protein as disclosed herein. Thus, the presence of the gene may be detected by assays based on the physical, chemical, immunological, or functional properties of its expressed product.

The present invention also relates to cloning vectors containing genes encoding analogs and derivatives of NRIF3 of the invention. The production and use of derivatives and analogs related to NRIF3 are within the scope of the present invention. For example, a deletion variant form of functional NRIF3 can be provided. In a specific embodiment, the derivative or analog is functionally active, i.e., capable of exhibiting one or more functional activities associated with a full-length, wild-type NRIF3 of the invention, or potentially blocking such function. Such functions include receptor binding activation or inhibition and localization to the cell nucleus. In another embodiment, an NRIF3 chimeric constructs fused with a non-NRIF3 protein are also contemplated. Examples of fusion partners include chimeric B42, GFP fusions, Gal4 fusion extension, etc.

NRIF3 derivatives can be made by altering encoding nucleic acid sequences by substitutions, additions or deletions that provide for functionally-active molecules. Preferably, derivatives are made that have enhanced or increased functional activity relative to native NRIF3. Alternatively, such derivatives may encode dominant-negative fragments of NRIF3 that contain the receptor binding domain that have the same or greater affinity for receptor.

Due to the degeneracy of nucleotide coding sequences, other DNA sequences which encode substantially the same amino acid sequence as a NRIF3 gene may be used in the practice of the present invention. These include but are not limited to allelic genes and nucleotide sequences comprising all or portions of NRIF3 genes which are altered by the substitution of different codons that encode the same amino acid residue within the sequence, thus producing a silent change. Likewise, the NRIF3 derivatives of the invention include, but are not limited to, those containing, as a primary amino acid sequence, all or part of the amino acid sequence of a NRIF3 protein including altered sequences in which functionally equivalent amino acid residues are substituted for residues within the sequence resulting in a conservative amino acid substitution. For example, one or more amino acid residues within the sequence can be substituted by another amino acid of a similar polarity and, if present, charge, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point. Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $CONH_2$ can be maintained.

Amino acid substitutions may also be introduced to substitute an amino acid with a particularly preferable property. For example, a Cys may be introduced a potential site for disulfide bridges with another Cys.

The genes encoding NRIF3 derivatives and analogs of the invention can be produced by various methods known in the art. The manipulations which result in their production can occur at the gene or protein level. For example, the cloned NRIF3 gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of NRIF3, care should be taken to ensure that the modified gene remains within the same translational reading frame as the NRIF3 gene, uninterrupted by translational stop signals, in the gene region where the desired activity is encoded.

Additionally, the NRIF3-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. In the Examples, infra, such modifications were made to introduce restriction sites and facilitate cloning the NRIF3 gene into an expression vector. Any technique for mutagenesis known in the art can be used, including but not limited to, in vitro site-directed mutagenesis (Hutchinson, C., et al., J. Biol. Chem. 253:6551, 1978; Zoller and Smith, DNA 3:479–488, 1984; Oliphant et al., Gene 44:177, 1986; Hutchinson et al., Proc. Natl. Acad. Sci. U.S.A. 83:710, 1986), use of TAB linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences.

Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2 $\mu$ plasmid.

Expression of NRIF3 Polypeptides

The nucleotide sequence coding for NRIF3, or antigenic fragment, derivative or analog thereof, or a functionally active derivative, including a chimeric protein, thereof, can be inserted into an appropriate expression vector, i.e., a vector which contains the necessary elements for the transcription and translation of the inserted protein-coding sequence. Thus, the nucleic acid encoding NRIF3 of the invention is operationally associated with a promoter in an expression vector of the invention. Both cDNA and genomic sequences can be cloned and expressed under control of such regulatory sequences. An expression vector also preferably includes a replication origin.

Alternatively, an NRIF3 polypeptide of the invention can be prepared using well-known techniques in peptide synthesis, including solid phase synthesis (using, e.g., BOC of FMOC chemistry), or peptide condensation techniques.

As used herein, the terms "polypeptide" and "protein" may be used interchangably to refer to the gene product (or corresponding synthetic product) of an NRIF3 gene. The term "protein" may also refer specifically to the polypeptide as expressed in cells. A peptide is generally a fragment of a polypeptide, e.g., of about six or more amino acid residues.

The necessary transcriptional and translational signals can be provided on a recombinant expression vector, or they may be supplied by the native gene encoding NRIF3 and/or its flanking regions.

Potential host-vector systems include but are not limited to mammalian cell systems infected with virus (e.g., vaccinia virus, adenovirus, adeno-associated virus, herpes virus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. A preferred expression host is a eukaryotic cell (e.g., yeast, insect, or mammalian cell). More preferred is a mammalian cell, e.g., human, rat, monkey, dog, or hamster cell.

A recombinant NRIF3 protein of the invention, or functional fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989, supra).

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of NRIF3 protein may be controlled by any promoter/enhancer element known in the art, but these regulatory elements must be functional in the host selected for expression. Promoters which may be used to control NRIF3 gene expression include, but are not limited to, cytomegalovirus (CMV) promoter (U.S. Pat. Nos. 5,385,839 and 5,168,062), the SV40 early promoter region (Benoist and Chambon, 1981, Nature 290:304–310), the promoter contained in the 3' long terminal repeat of Rous sarcoma virus (Yamamoto, et al., Cell 22:787–797, 1980), the herpes thymidine kinase promoter (Wagner et al., Proc. Natl. Acad. Sci. U.S.A. 78:1441–1445, 1981), the regulatory sequences of the metallothionein gene (Brinster et al., Nature 296:39–42, 1982); prokaryotic expression vectors such as the β-lactamase promoter (Villa-Kamaroff, et al., Proc. Natl. Acad. Sci. U.S.A. 75:3727–3731, 1978), or the tac promoter (DeBoer, et al., Proc. Natl. Acad. Sci. U.S.A. 80:21–25, 1983); see also "Useful proteins from recombinant bacteria" in Scientific American, 242:74–94, 1980; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., Cell 38:639–646, 1984; Ornitz el al., Cold Spring Harbor Symp. Quant. Biol. 50:399–409, 1986; MacDonald, Hepatology 7:425–515, 1987); insulin gene control region which is active in pancreatic beta cells (Hanahan, Nature 315:115–122, 1985), immunoglobulin gene control region which is active in lymphoid cells (Grosschedl et al., Cell 38:647–658, 1984; Adames et al., Nature 318:533–538, 1985; Alexander et al., Mol. Cell. Biol. 7:1436–1444, 1987), mouse mammary tumor virus control region which is active in testicular, breast, lymphoid and mast cells (Leder et al., Cell 45:485–495, 1986), albumin gene control region which is active in liver (Pinkert et al., Genes and Devel. 1:268–276, 1987), alpha-fetoprotein gene control region which is active in liver (Krumlauf et al., Mol. Cell. Biol. 5:1639–1648, 1985; Hammer et al., Science 235:53–58, 1987), alpha 1-antitrypsin gene control region which is active in the liver (Kelsey et al., Genes and Devel. 1:161–171, 1987), beta-globin gene control region which is active in myeloid cells (Mogram et al., Nature 315:338–340, 1985; Kollias et al., Cell 46:89–94, 1986), myelin basic protein gene control region which is active in oligodendrocyte cells in the brain (Readhead et al., Cell 48:703–712, 1987), myosin light chain-2 gene. control region which is active in skeletal muscle (Sani, Nature 314:283–286, 1985), and gonadotropic releasing hormone gene control region which is active in the hypothalamus (Mason et al., Science 234:1372–1378, 1986).

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMal-C2, pET, pGEX (Smith et al., Gene 67:31–40, 1988), pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2 μ plasmid or derivatives thereof, vectors useful in eukaryotic cells, such as vectors useful in insect or mammalian cells; vectors derived from combinations of plasmids and phage DNAs, such as plasmids that have been modified to employ phage DNA or other expression control sequences; and the like.

Yeast expression systems can also be used according to the invention to express NRIF3. For example, the non-fusion pYES2 vector (XbaI, SphI, ShoI, NotI, GstXI, EcoRI, BstXI, BamHI, SacI, KpnI, and HindIII cloning sites; Invitrogen) or the fusion pYESHisA, B, C (XbaI, SphI, ShoI, NotI, BstXI, EcoRI, BamHI, SacI, KpnI, and HindIII cloning sites, N-terminal peptide purified with ProBond resin and cleaved with enterokinase; Invitrogen), to mention just two, can be employed according to the invention. As exemplified infra, a yeast two-hybrid expression system can be prepared in accordance with the invention.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., J. Biol. Chem. 267:963–967, 1992; Wu and Wu, J. Biol. Chem. 263:14621–14624, 1988; Hartmut et al., Canadian Patent Application No. 2,012,311, filed Mar. 15, 1990).

Antibodies to NRIF3

According to the invention, NRIF3 polypeptides produced recombinantly or by chemical synthesis, and fragments or other derivatives or analogs thereof, including fusion proteins, may be used as an immunogen to generate antibodies that recognize the NRIF3 polypeptide. Such antibodies include but are not limited to polyclonal, monoclonal, chimeric, single chain, Fab fragments, and an Fab expression library. Such an antibody is specific for human NRIF3.

Various procedures known in the art may be used for the production of polyclonal antibodies to NRIF3 polypeptide or derivative or analog thereof. For the production of antibody, various host animals can be immunized by injection with the NRIF3 polypeptide, or a derivative (e.g., fragment or fusion protein) thereof, including but not limited to rabbits, mice, rats, sheep, goats, etc. In one embodiment, the NRIF3 polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the NRIF3 polypeptide, or fragment, analog, or derivative thereof, any technique that provides for the production of antibody molecules by continuous cell lines in culture may be used. These include but are not limited to the hybridoma technique originally developed by Kohler and Milstein (Nature 256:495–497, 1975), as well as the trioma technique, the human B-cell hybridoma technique (Kozbor et al., Immunology Today 4:72, 1983; Cote et al., Proc. Natl. Acad. Sci. U.S.A. 80:2026–2030, 1983), and the EBV-hybridoma technique to produce human monoclonal antibodies (Cole et al., in Monoclonal Antibodies and Cancer Therapy, Alan R. Liss, Inc., pp. 77–96, 1985). Production of human antibodies by CDR grafting is described in U.S. Pat. Nos. 5,585,089, 5,693,761, and 5,693,762 to Queen et al., and also in U.S. Pat. No. 5,225,539 to Winter and International Patent Application PCT/WO91/09967 by Adau et al. In an additional embodiment of the invention, monoclonal antibodies can be produced in germ-free animals (International Patent Publication No. WO89/12690, published Dec. 28, 1989). In fact, according to the invention, techniques developed for the production of "chimeric antibodies" (Morrison et al., J. Bacteriol. 159:870, 1984); Neuberger et al., Nature 312:604–608, 1984; Takeda et al., Nature 314:452–454, 1985) by splicing the genes from a mouse antibody molecule specific for an NRIF3 polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. Nos. 5,476, 786 and 5,132,405 to Huston; U.S. Pat. No. 4,946,778) can be adapted to produce NRIF3 polypeptide-specific single chain antibodies. An additional embodiment of the invention utilizes the techniques described for the construction of Fab expression libraries (Huse et al., Science 246:1275–1281, 1989) to allow rapid and easy identification of monoclonal Fab fragments with the desired specificity for an NRIF3 polypeptide, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an NRIF3 polypeptide, one may assay generated hybridomas for a product which binds to an NRIF3 polypeptide fragment containing such epitope. For selection of an antibody specific to an NRIF3 polypeptide from a particular species of animal, one can select on the basis of positive binding with NRIF3 polypeptide expressed by or isolated from cells of that species of animal.

The foregoing antibodies can be used in methods known in the art relating to the localization and activity of the NRIF3 polypeptide, e.g., for Western blotting, imaging NRIF3 polypeptide in situ, measuring levels thereof in appropriate physiological samples, etc. using any of the detection techniques mentioned above or known in the art. Such antibodies can be used to identify proteins that interact with NRIF3.

In a specific embodiment, antibodies that agonize or antagonize the activity of NRIF3 polypeptide can be generated. They can also be used to regulate or inhibit NRIF3 activity intracellular, i.e., the invention contemplates an intracellular antibody (intrabody), e.g., single chain Fv antibodies (see generally, Chen, Mol. Med. Today, 3:160–167, 1997; Spitz et al., Anticancer Res., 16:3415–3422, 1996; Indolfi et al., Nat. Med., 2:634–635, 1996; Kijima et al., Pharmacol. Ther., 68:247–267, 1995).

Screening and Chemistry

Identification and isolation of NRIF3 provides for development of screening assays, particularly for high throughput screening of molecules that up- or down-regulate the activity of NRIF3, e.g., by permitting expression of NRIF3 in quantities greater than can be isolated from natural sources, or in indicator cells that are specially engineered to indicate the activity of NRIF3 expressed after transfection or transformation of the cells. In addition, the present invention contemplates methods for identifying specific ligands of thyroid hormone receptor or retinoid X receptor using various screening assays known in the art.

Any screening technique known in the art can be used to screen for NRIF3 agonists or antagonists. The present invention contemplates screens for small molecule ligands or ligand analogs and mimics, as well as screens for natural ligands that bind to and agonize or antagonize the activity of NRIF3 in vivo. For example, natural products libraries can be screened using assays of the invention for molecules that agonize or antagonize NRIF3 activity.

As used herein, the term "ligand" refers to compounds.

Knowledge of the primary sequence of the protein, and the similarity of that sequence with proteins of known function, can provide an initial clue as to the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" (Scott and Smith, Science 249:386–390, 1990; Cwirla, et al., Proc. Natl. Acad. Sci., 87:6378–6382, 1990; Devlin et al., Science, 49:404–406, 1990), very large libraries can be constructed ($10^6$–$10^8$ chemical entities). A second approach uses primarily chemical methods, of which the Geysen method (Geysen et al., Molecular Immunology 23:709–715, 1986; Geysen et al. J. Immunologic Method 102:259–274, 1987; and the method of Fodor et al. (Science 251:767–773, 1991) are examples. Furka et al. (14th International Congress of Biochemistry, Volume #5, Abstract FR:013, 1988; Furka, Int. J. Peptide Protein Res. 37:487–493, 1991), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists.

In another aspect, synthetic libraries (Needels et al., Proc. Natl. Acad. Sci. USA 90:10700–4, 1993; Ohlmeyer et al., Proc. Natl. Acad. Sci. USA 90:10922–10926, 1993; Lam et al., International Patent Publication No. WO92/00252; Kocis et al., International Patent Publication No. WO9428028) and the like can be used to screen for NRIF3 ligands according to the present invention.

Screening System for TR and RXR Agonists and Antagonists

In a specific embodiment, in addition to directly screening for molecules that directly interact with NRIF3, such as antibodies or small molecules, which can serve as negative regulators (or even positive regulators) of NRIF3 activity, the present invention provides the components to reconstitute thyroid hormone receptor and retinoid-X receptor signaling activity in whole or in part. This reconstituted system, which depends on recombinant expression of TR and RXR with NRIF3 in a host cell, permits discovery and evaluation of agonists and antagonists of receptor signally (a signal-inducing ligand is an agonist; a non-signal inducing ligand is an antagonist). Such agonists and antagonist can act at the level of TR or RXR binding, i.e., as receptor ligands, or at the level of signal transduction. Modulation of signal transduction can occur by modulating (inhibiting or promoting) receptor-coactivator (NRIF3) interaction, or NRIF3 activity, through binding to NRIF3 and/or receptor.

Any host cell that provides for expression of functional TR or RXR and NRIF3 proteins can be used, e.g., a eukaryotic cell. In a specific embodiment, the yeast system described in the examples can be modified for use in a screening assay of this sort. Alternatively, one can employ a mammalian or insect cells genetically engineered to express the TR or RXR and NRIF3 proteins. In a specific embodiment, a host cell harbors a construct that expresses a nuclear hormone receptor (TR or RXR or its ligand binding domain) fused to a DNA binding domain and another construct expressing NIRF3 fused to an activation domain. Alternatively, the host cell harbors a construct expressing NRIF3 fused to a DNA binding domain and another construct expressing a receptor (TR or RXR or a ligand-binding domain thereof) fused to an activation domain. The host cell will also include a reporter gene that is expressed in response to binding of the nuclear hormone receptor-NRIF3 complex (formed as a result of binding of ligand to the nuclear hormone receptor) to an expression control sequence operatively associated with the reporter gene. Reporter genes for use in the invention encode detectable proteins, including, but by no means limited to, chloramphenicol transferase (CAT), β-galactosidase (β-gal), luciferase, green fluorescent protein (GFP), alkaline phosphatase, and other genes that can be detected, e.g., immunologically (by antibody assay). GFP has been modified to produce proteins that remain functional but have different fluorescent properties. Heim et al (U.S. Pat. No. 5,625,048) modified GFP resulting in amino-acid changes which exhibited different excitation and emission spectra with visibly distinct colors and increased intensities of emission. Bjorn et al (WO9623898) developed a new construct which encoded a modified GFP but also contained an enzyme recognition site. Bjorn et al (WO9711094) also developed new fluorescent proteins with increased intensity compared to the parent proteins. Hauswirth et al (WO97266333) developed a GFP protein optimized to provide higher levels of expression in mammalian cells. Gaitanaris et al (WO9742320) modified GFP resulting to increase the intensity of fluorescence, e.g., by some twenty times greater than wild-type GFP, therefore increasing the sensitivity of detection. Cubitt et al (WO9806737) developed modified GFP which could be easily distinguished from the already known green and blue fluorescent proteins. Evans et al (WO9821355) developed new GFP mutants excitable with blue and white light.

The host cell screening system of the invention permits two kinds of assays: direct activation assays (agonist screen) and inhibition assays (antagonist screen). An agonist screen involves detecting expression of the reporter gene by the host cell contacted with a test compound. If the reporter gene is expressed, the test compound has induced association of the nuclear receptor and NRIF3, and the test compound is a candidate agonist of the nuclear receptor signal. If there is no or very low expression of the reporter gene, no such association and gene activation has occurred, and the test compound is not an effective agonist.

An antagonist screen involves detecting expression of the reporter gene by the host cell when contacted with the nuclear hormone receptor ligand (or another agonist) and a test compound. If reporter gene expression is reduced or eliminated, the test compound has prevented activation of gene expression, which may occur by competitively or non-competitively inhibiting binding of the ligand (or agonist) to the nuclear hormone receptor; preventing association of the receptor and NRIF3. Such a test compound is a candidate antagonist of nuclear hormone receptor signaling. If there is no change in expression of the reporter gene, the test compound is not an effective antagonist.

The reporter gene assay system described here may be used in a high-throughput primary screen for agonists and antagonists, or it may be used as a secondary functional screen for candidate compounds identified by a different primary screen, e.g., a binding assay screen that identifies compounds that interact with the receptor and/or NRIF3.

Modulation of NRIF3 Activity

Since NRIF3 is a co-activator of the thyroid hormone receptors (TRs) and the retinoid X receptors (RXRs), a defect in the NRIF3 function (e.g., caused by genetic mutations) can result in defects in one or both of these two receptor-signalling pathways. For example, a defect in NRIF3 may lead to a weakened response to thyroid hormones and, therefore, results in functional hypothyroidism. In addition to their roles in the retinoid signalling, the RXRs are involved in the function of many other nuclear receptors through heterodimerization with these receptors. In a number of such heterodimers, the RXR partner is capable of binding its ligand and, therefore, regulating the expression of the target genes in conjunction with the other receptor. Therefore, a defect in the NRIF3 may (i) affect the retinoid signalling and lead to an abnormal response to vitamin A; or (ii) affect other physiological processes that are (partially) regulated by RXRs through the heterodimerization with other receptors. An example of such a heterodimer is PPARγ/RXR, which has been an important target for developing drugs for the treatment of type II diabetes. It has been shown in clinical and in experimental model systems that ligands for both PPARγ and RXR can sensitize the response to insulin and, therefore, have therapeutic values for type II diabetes, presumably through up-regulation of target genes that are important in mediating insulin signalling. It is an interesting possibility that a defect in NRIF3 may weaken the signalling of the PPARγ/RXR heterodimer in vivo and may contribute to the development of type II diabetes and lead to weakened response to drugs that target the PPARγ/RXR heterodimer.

In the case when a defect in NRIF3 causes the disease phenotype (such as the diseases discussed in the above paragraph), one of the therapeutic options would be to correct such a defect through the introduction of a functional NRIF3 (e.g., by using a NRIF3 gene therapy). As discussed above, such diseases may include functional hypothyroidism, abnormal response to vitamin A, and type II diabetes.

On the other hand, even if the endogenous NRIF3 is not defective and the disease is not directly related to NRIF3, NRIF3 still be used in the treatment of such a disease if up-regulation of the corresponding hormone signalling pathways would be beneficial. For example, even when the hypothyroidism or type II diabetes are not caused by a defect in NRIF3, additional expression of NRIF3 would enhance the corresponding hormone signalling pathways and, therefore, could be used to treat the diseases (either alone or in conjunction with other drugs that also up-regulate the targeted hormone pathways).

Retinoids have been shown to inhibit the growth and/or induce differentiation of a number of cancer cells. Retinoid signalling is mediated by the RAR/RXR heterodimer. When the RAR partner is occupied by its ligand, the RXR becomes a permissive partner and can engage in its own ligand binding and subsequent signalling. In such a case it is possible that the additional introduction of NRIF3 would enhance the signal output from an activated RAR/RXR heterodimer and thus potentiate the effect of the retinoids in inhibiting the growth of cancer cells and/or in inducing their differentiation. In addition, certain breast cancer cells are resistant to RAR agonists. However, treatment with RXR-specific ligands can inhibit the growth of these cells and/or induce their sensitivities to RAR agonists. In such a case, the introduction of NRIF3 may enhance the anti-cancer effect of RXR-specific ligands. In summary, NRIF3 can be used in treating cancers in conjunction with retinoids and/or rexinoids.

RXR-specific ligands have also been shown to be efficient chemoprevention agents for cancers and type II diabetes in experimental models systems. The introduction of NRIF3 would further enhance the effects of such RXR ligands in preventing the onset of these diseases. Finally, since RXRs are also involved in many other receptor-signalling pathways, NRIF3 may have therapeutic potentials in diseases related to such receptors as well.

In the case of a disease that is caused by "over-signalling" (e.g., hyperthyroidism) of a certain hormone pathway that involves NRIF3, it will be of therapeutic benefit to down-regulate the pathway by targeting endogenous NRIF3. There are several different ways to target NRIF3: (i) through the introduction of antisense oligonucleotides against NRIF3; (ii) through suitable modification of NRIF3 to create a dominant negative construct (if applicable); (iii) through neutralizing anti-NRIF3 intrabodies; and (iv) through small molecules that mimic NRIF3 in its binding to the liganded receptor, but do not relay the activation signal(s).

In vivo Testing Using Transgenic Animals

Transgenic mammals can be prepared for evaluating the molecular mechanisms of NRIF3, and particularly human NRIF3/TR- or NRIF3/RXR-induced signaling. Such mammals provide excellent models for screening or testing drug candidates. It is possible to evaluate compounds or diseases on "knockout" animals, e.g., to identify a compound that can compensate for a defect in NRIF3 activity. Alternatively, human NRIF3 or TR/RXR, or both (double transgenics), "knock-in" mammals can be prepared for evaluating the molecular biology of this system in greater detail than is possible with human subjects (although the close evolutionary relationship of TR and RXR likely obviate the need to use the human forms of these receptors. Both technologies permit manipulation of single units of genetic information in their natural position in a cell genome and to examine the results of that manipulation in the background of a terminally differentiated organism. These animals can be evaluated for hyperthyroidism, hypothyroidism, or susceptibility to diabetes cancer, e.g., in response to challenge of carcinogens, by increasing or decreasing RXR response).

A "knockout mammal" is a mammal (e.g., mouse) that contains within its genome a specific gene that has been inactivated by the method of gene targeting (see, e.g., U.S. Pat. No. 5,777,195 and U.S. Pat. No. 5,616,491). A knockout mammal includes both a heterozygote knockout (i.e., one defective allele and one wild-type allele) and a homozygous mutant. Preparation of a knockout mammal requires first introducing a nucleic acid construct that will be used to suppress expression of a particular gene into an undifferentiated cell type termed an embryonic stem cell. This cell is then injected into a mammalian embryo. A mammalian embryo with an integrated cell is then implanted into a foster mother for the duration of gestation. Zhou, et al. (Genes and Development, 9:2623–34, 1995) describes PPCA knock-out mice. Knockout mice can be used to study hypothyroidism, vitamin A responses, type II diabetes, and cancer susceptibility. Disease phenotypes that develop can provide a platform for further drug discovery.

The term "knockout" refers to partial or complete suppression of the expression of at least a portion of a protein encoded by an endogenous DNA sequence in a cell. The term "knockout construct" refers to a nucleic acid sequence that is designed to decrease or suppress expression of a protein encoded by endogenous DNA sequences in a cell. The nucleic acid sequence used as the knockout construct is typically comprised of (1) DNA from some portion of the gene (exon sequence, intron sequence, and/or promoter sequence) to be suppressed and (2) a marker sequence used to detect the presence of the knockout construct in the cell. The knockout construct is inserted into a cell, and integrates with the genomic DNA of the cell in such a position so as to prevent or interrupt transcription of the native DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA). The knockout construct nucleic acid sequence may comprise 1) a full or partial sequence of one or more exons and/or introns of the gene to be suppressed, 2) a full or partial promoter sequence of the gene to be suppressed, or 3) combinations thereof. Typically, the knockout construct is inserted into an embryonic stem cell (ES cell) and is integrated into the ES cell genomic DNA, usually by the process of homologous recombination. This ES cell is then injected into, and integrates with, the developing embryo.

The phrases "disruption of the gene" and "gene disruption" refer to insertion of a nucleic acid sequence into one region of the native DNA sequence (usually one or more exons) and/or the promoter region of a gene so as to decrease or prevent expression of that gene in the cell as compared to the wild-type or naturally occurring sequence of the gene. By way of example, a nucleic acid construct can be prepared containing a DNA sequence encoding an antibiotic resistance gene which is inserted into the DNA sequence that is complementary to the DNA sequence (promoter and/or coding region) to be disrupted. When this nucleic acid construct is then transfected into a cell, the construct will integrate into the genomic DNA. Thus, many progeny of the cell will no longer express the gene at least in some cells, or will express it at a decreased level, as the DNA is now disrupted by the antibiotic resistance gene.

A "knock-in" mammal is a mammal in which an endogenous gene is substituted with a heterologous gene (Roemer et al., New Biol. 3:331, 1991). Preferably, the heterologous gene is "knocked-in" to a locus of interest, either the subject of evaluation(in which case the gene may be a reporter gene; see Elefanty et al., Proc Natl Acad Sci USA 95:11897, 1998) of expression or function of a homologous gene, thereby linking the heterologous gene expression to transcription from the appropriate promoter. This can be achieved by homologous recombination, transposon (Westphal and Leder, Curr Biol 7:530, 1997), using mutant recombination sites (Araki et al., Nucleic Acids Res 25:868, 1997) or PCR (Zhang and Henderson, Biotechniques 25:784, 1998).

Generally, for homologous recombination, the DNA will be at least about 1 kilobase (kb) in length and preferably 3–4 kb in length, thereby providing sufficient complementary sequence for recombination when the knockout construct is introduced into the genomic DNA of the ES cell (discussed below).

Included within the scope of this invention is a mammal in which two or more genes have been knocked out or knocked in, or both. Such mammals can be generated by repeating the procedures set forth herein for generating each knockout construct, or by breeding to mammals, each with a single gene knocked out, to each other, and screening for those with the double knockout genotype.

Regulated knockout animals can be prepared using various systems, such as the tet-repressor system (see U.S. Pat. No. 5,654,168) or the Cre-Lox system (see U.S. Pat. No. 4,959,317 and U.S. Pat. No. 5,801,030).

In another series of embodiments, transgenic animals are created in which (i) a human NRIF3 is stably inserted into the genome of the transgenic animal; and/or (ii) the endogenous NRIF3 genes are inactivated and replaced with their human counterparts. See, e.g., Coffman, Semin. Nephrol. 17:404, 1997; Esther et al., Lab. Invest. 74:953, 1996; Murakami et al., Blood Press. Suppl. 2:36, 1996. Such animals can be treated with candidate compounds and monitored for the effects of such drugs on NRIF3 activity.

Gene Therapy to Modulate NRIF3 Actvity

A gene encoding NRIF3, or alternatively a negative regulator of NRIF3 such as an antisense nucleic acid, intracellular antibody (intrabody), or dominant negative NIRF3 (which may be truncated), can be introduced in vivo, ex vivo, or in vitro using a viral or a non-viral vector, e.g., as discussed above. Expression in targeted tissues can be effected by targeting the transgenic vector to specific cells, such as with a viral vector or a receptor ligand, or by using a tissue-specific promoter, or both. Targeted gene delivery is described in International Patent Publication WO95/28494, published October 1995.

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interieukin-12 (IL-12), interferon-γ (IFN-γ), or anti-CD4 antibody, can be administered to block humoral or cellular immune responses to the viral vectors (see, e.g., Wilson, Nature Medicine, 1995). In that regard, it is advantageous to employ a viral vector that is engineered to express a minimal number of antigens.

Adenovirus vectors. Adenoviruses are eukaryotic DNA viruses that can be modified to efficiently deliver a nucleic acid of the invention to a variety of cell types in vivo, and has been used extensively in gene therapy protocols. Various serotypes of adenovirus exist. Of these serotypes, preference is given to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: Mav1, Beard et al., Virology 75 (1990) 81), ovine, porcine, avian, and simian (example: SAV) origin. Preferably, the adenovirus of animal origin is a canine adenovirus, more preferably a CAV2 adenovirus (e.g., Manhattan or A26/61 strain (ATCC VR-800), for example). Various replication defective adenovirus and minimum adenovirus vectors have been described for gene therapy (WO94/26914, WO95/02697, WO94/28938, WO94/28152, WO94/12649, WO95/02697 WO96/22378). The replication defective recombinant adenoviruses according to the invention can be prepared by any technique known to the person skilled in the art (Levrero et al., Gene 101:195 1991; EP 185 573; Graham, EMBO J. 3:2917, 1984; Graham et al., J. Gen. Virol. 36:59 1977). Recombinant adenoviruses are recovered and purified using standard molecular biological techniques, which are well known to one of ordinary skill in the art.

Adeno-associated viruses. The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterized. The use of vectors derived from the AAVs for transferring genes in vitro and in vivo has been described (see WO91/18088; WO93/09239; U.S. Pat. No. 4,797,368, U.S. Pat. No. 5,139,941, EP 488 528). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (for example an adenovirus). The AAV recombinants which are produced are then purified by standard techniques.

Retrovirus vectors. In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; EP 453242, EP178220; Bernstein et al. Genet. Eng. 7 (1985) 235; McCormick, BioTechnology 3 (1985) 689; International Patent Publication No. WO95/07358, published Mar. 16, 1995, by Dougherty et al; and Kuo et al., 1993, Blood 82:845. The retroviruses are integrating viruses which infect dividing cells. The retrovirus genome-includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as MoMuLV ("murine Moloney leukaemia virus"), MSV ("murine Moloney sarcoma virus"), HaSV ("Harvey sarcoma virus"); SNV ("spleen necrosis virus"); RSV ("Rous sarcoma virus") and Friend virus. Suitable packaging cell lines have been described in the prior art, in particular the cell line PA317 (U.S. Pat. No. 4,861,719); the PsiCRIP cell line (WO90/02806) and the GP+envAm-12 cell line (WO89/07150). In addition, the recombinant retroviral vectors can contain modifications within the LTRs for suppressing transcriptional activity as well as extensive encapsidation sequences which may include a part of the gag gene (Bender et al., J. Virol. 61:1639, 1987). Recombinant retroviral vectors are purified by standard techniques known to those having ordinary skill in the art.

Retrovirus vectors can also be introduced by recombinant DNA viruses, which permits one cycle of retroviral replication and amplifies transfection efficiency (see WO95/22617, WO95/26411, WO96/39036, WO97/19182).

Lentivirus vectors. In another embodiment, lentiviral vectors are can be used as agents for the direct delivery and sustained expression of a transgene in several tissue types, including brain, retina, muscle, liver and blood. The vectors can efficiently transduce dividing and nondividing cells in these tissues, and maintain long-term expression of the gene of interest. For a review, see, Naldini, Curr. Opin. Biotechnol., 9:457–63, 1998; see also Zufferey, et al., J. Virol., 72:9873–80, 1998). Lentiviral packaging cell lines are available and known generally in the art. They facilitate the production of high-titer lentivirus vectors for gene therapy. An example is a tetracycline-inducible VSV-G pseudotyped lentivirus packaging cell line which can generate virus particles at titers greater than 106 IU/ml for at least 3 to 4 days (Kafri, el al., J. Virol., 73:576–584, 1999). The vector produced by the inducible cell line can be concentrated as needed for efficiently transducing nondividing cells in vitro and in vivo.

Non-viral vectors. A vector can be introduced in vivo in a non-viral vector, e.g., by lipofection, with other transfection facilitating agents (peptides, polymers, etc.), or as naked DNA. Synthetic cationic lipids can be used to prepare liposomes for in vivo transfection, with targeting in some instances (Feigner, et. al., Proc. Natl. Acad. Sci. U.S.A. 84:7413–7417, 1987; Feigner and Ringold, Science 337:387–388, 1989; see Mackey, et al., Proc. Natl. Acad. Sci. U.S.A. 85:8027–8031, 1988; Ulmer et al., Science 259:1745–1748, 1993). Useful lipid compounds and compositions for transfer of nucleic acids are described in International Patent Publications WO95/18863 and WO96/17823, and in U.S. Pat. No. 5,459,127. Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931). Recently, a relatively low voltage, high efficiency in vivo DNA transfer technique, termed electrotransfer, has been described (Mir et al., C.P. Acad. Sci., 321:893, 1998; WO99/01157; WO99/01158; WO99/01175). DNA vectors for gene therapy can be introduced into the desired host cells by methods known in the art, e.g., electroporation, microinjection, cell fusion, DEAE dextran, calcium phosphate precipitation, use of a gene gun (ballistic transfection), or use of a DNA vector transporter (see, e.g., Wu et al., J. Biol. Chem. 267:963–967, 1992; Wu and Wu, J. Biol. Chem. 263:14621–14624, 1988; Hartmut et al., Canadian Patent Application No. 2,012,311, filed Mar. 15, 1990; Williams et al., Proc. Natl. Acad. Sci. USA 88:2726–2730, 1991). Receptor-mediated DNA delivery approaches can also be used (Curiel et al., Hum. Gene Ther. 3:147–154, 1992; Wu and Wu, J. Biol. Chem. 262:4429–4432, 1987). U.S. Pat. Nos. 5,580,859 and 5,589,466 disclose delivery of exogenous DNA sequences, free of transfection facilitating agents, in a mammal.

EXAMPLES

The present invention will be better understood by reference to the following examples, which are provided by way of exemplification and are not intended to limit the invention.

Example 1

Identification and Characterization of NRIF3

To further our understanding of the molecular events underlying receptor-activated transcription, we sought to identify additional co-activators using a yeast two-hybrid screening strategy (29). This Example describes the isolation of a novel co-activator for nuclear receptors, designated as NRIF3. Fluorescence microscopy indicates that NRIF3 is a nuclear protein. The yeast two-hybrid and in vitro binding assays revealed that NRF3 interacts specifically with TR and RXR in a ligand-dependent fashion but does not interact with other examined nuclear receptors. Transfection studies indicate that NRIF3 selectively potentiates TR- and RXR-mediated transactivation in vivo. NRIF3 encodes a small protein of 177 amino acids and other than an N-terminal LxxLL (SEQ ID NO:1) motif shares no homology with known co-activators. The combination of computer modeling, domain and mutagenesis analyses suggest that NRIF3 interacts with nuclear receptors through its C-terminal domain that contains a novel LxxIL (SEQ ID NO:2) module, while other part of NRIF3 may contribute to its observed receptor specificity. These findings may provide novel insight into the molecular mechanism(s) of receptor-mediated transcriptional activation as well as the functional specificity of nuclear receptors.

Materials and Methods

Isolation of NRIFs and the yeast two-hybrid assay. The Brent two-hybrid system (29) was employed to isolate candidate cDNA clones interacting with LexA-TRα in a ligand-dependent fashion. Full length chicken TRα (cTRα) was fused in frame to the C-terminus of the LexA DBD in pEG202 (29). The LexA-TRα bait, the LacZ reporter (pSH18-34), and a pJG4-5 based HeLa cell cDNA library were transformed into the yeast strain EGY48 (29). The transformants were selected on Gal/Raf/X-gal medium in the absence of leucine and were further screened for the expression of LacZ in the presence of 1 μM T3. Blue colonies were picked and re-examined for T3-dependent expression of LacZ. Positive yeast clones were then selected and plasmids harboring candidate prey cDNAs were isolated. Individual candidate prey plasmid was then amplified in E. coli and re-transformed into the original yeast strain to confirm the interaction phenotype. The cDNA inserts were then sequenced using an automatic sequencer. Four novel clones (NRIF1, 2, 3, and 4) were obtained. Among them, NRIF3 was a full length clone.

Wild type NRIF3, the endonexin long form (EnL) and short form (EnS), and the L9A NRIF3 mutant were examined for their interaction with various nuclear receptors in a yeast two-hybrid assay. The following receptor baits were used: LexA-cTRα LBD, LexA-hTRβ LBD, LexA-hRARα LBD, LexA-hRXRα LBD, and LexA-hGR LBD. The NRIF3 C-terminal domain (NCD) was fused in frame with the LexA DBD and examined for interaction with receptor LBDs using the following preys: B42-cTRα LBD, B42-hRARα LBD, and B42-hRXRα LBD expressed from pJG4-5. Yeast cells harboring appropriate plasmids were grown in selective media with Gal/Raf in the presence or absence of cognate ligand (1 μM T3 for TR, all trans or 9-cis RA for RAR, 9-cis RA for RXR, and 10 μM deoxycorticosterone for GR) overnight before β-galactosidase activity was assayed using o-Nitrophenyl β-D-Galactopyranoside as the substrate. β-galactosidase units are expressed as (O.D. 420 nm×1000)/(minutes of incubation×O.D. 600 nm of yeast suspension).

Fluorescence Microscopy. Full length NRIF3 was cloned into the GFP fusion protein expression vector pEGFP (Clontech). The resulting GFP-NRIF3 vector and the control plasmid pEGFP were transfected into HeLa cells by calcium phosphate co-precipitation. Cells were incubated at 37° C. for 24 hours before the examination with a fluorescence microscope to determine the subcellular location of GFP-NRIF3 or the GFP control.

In vitro binding assay. Full length NRIF3 was cloned into pGEX2T, a bacterial GST-fusion protein expression vector (Pharmacia). The GST-NRIF3 fusion protein was expressed in E. coli and affinity purified using glutathione-agarose beads (30). $^{35}$S-labeled full length cTRα, hRARα, hRXRα, hVDR, hGR, hPR, and hER were generated by in vitro transcription/translation using a reticulocyte lysate system (Promega). Binding was performed as previously described (30), using the following buffer: 20 mM Hepes (pH 7.9), 1 mM $MgCl_2$, 1mM DTT, 10% Glycerol, 0.05% Triton X-100, 1 μM $ZnCl_2$, and 150 mM KCl. Appropriate ligands were added into the binding reaction when indicated: 1 μM T3 for TR, 1 μM all trans RA or 9-cis RA for RAR, 1 μM 9-cis RA for RXR, and 150 nM 1,25-$(OH)_2$ VitD3, dexamethathone, progesterone, or estradiol for VDR, GR, PR, or ER. After the binding reaction, the beads were washed three times and the labeled receptors bound to the beads were examined in 10% SDS-PAGE followed by autoradiography. Five percent of the $^{35}$S-labeled receptor input was also electrophoresed in the same gel.

Transfection studies. Most reporters used in this study have been described previously, including IR-ΔMTV-CAT, DR4-ΔMTV-CAT, GH-TRE-tk-CAT, IR+3 (ERE)-ΔMTV-CAT (5, 25, 78). A DRI-ΔMTV-CAT reporter responsive to RXR was obtained from Ron Evans. A GRE/PRE-tk-CAT reporter was obtained from Gunther Schutz. The (IR)2-TATA-CAT was constructed in our laboratory by cloning two copies of the IR sequence (AGGTCA TGACCT) upstream of a TATA element derived from the tk promoter. A hVDR expression vector and the VDRE-ΔMTV-CAT containing the VDRE from the osteocalcin promoter were obtained from J. Wesley Pike. Vectors expressing cTRα, hRARα, hRXRα, rGR, hPR, and hER have been described previously (17, 25, 26, 50, 53, 81). The NRIF3 expression vector was constructed by cloning full length NRIF3 into a pExpress vector (25). Appropriate plasmids were transfected into HeLa cells by calcium phosphate co-precipitation using 25–100 ng of the receptors, 250–500 ng of the CAT reporters, and 750 ng of the NRIF3 or control pExpress vector. After transfection, cells were incubated at 37° C. (with or without cognate ligands) for 42 hours before being harvested. CAT assays were carried out as previously described (30). Relative CAT activity was determined as the percent acetylation of substrate per 30 μg of cell protein in a 15 hour incubation at 37° C. The results were calculated from duplicate or quadruplicate samples and the variation among samples was less than 10%.

Domain and mutagenesis analyses. To construct pJG4-5 derived vectors expressing EnL or EnS, the pJG4-5/NRIF3 plasmid was digested with NcoI and XhoI, and the resulting vector fragment was gel-purified. This fragment was then ligated to an EnL or EnS insert generated from pExpress-EnL or pExpress-EnS by an NcoI/SalI double digest. The resulting pJG4-5/EnL or EnS plasmids were confirmed by sequence analysis. The L9A mutant form of NRIF3 was generated by site-directed mutagenesis using a PCR-based method, and the mutation was confirmed by sequence analysis. pJG4-5 derived vectors expressing EnL, EnS, or the L9A NRIF3 mutant form were transformed into yeast strains harboring the LacZ reporter (pSH18-34) and appropriate bait plasmids (LexA-TR, LexA-RAR, LexA-RXR, and LexA-GR). Transformants were subjected to quantitative assays of β-galactosidase activity as described earlier.

To construct the bait plasmid expressing LexA-NCD, a derivative of pEG202 (which contains a new polyLinker) plasmid was digested with NcoI and XhoI and ligated to synthetic oligonucleotides that encode the last 16 amino acids of NRIF3 (residues 162–177). Similarly, mutant NCD was generated by using oligonucleotides that contain the designed mutations in the ligation reaction. All constructs were confirmed by sequence analysis. Bait plasmids expressing LexA-NCD or LexA-mutant NCD were transformed together with one of these prey plasmids (B42-TR LBD, B42-RXR LBD, and B42-RAR LBD) into the yeast strain that harbors the LacZ reporter (pSH18-34). Subsequent two-hybrid assays were carried out as described earlier.

Docking of co-activator peptides to receptors. We built a model of the interaction between the 17-residue C-terminal peptide of NRIF3 (KASRHLDSYEFLKAILN; SEQ ID NO:7) and the LBDs of several receptors (TRα was used as an example in FIG. 10). An LxxIL (SEQ ID NO:2) motif within the NRIF3 peptide is underlined. A similar modeling procedure was carried out on a 20-residue peptide (SLTERHKILHRLLQEGSPSD; SEQ ID NO:8) of the second LxxLL (SEQ ID NO:1) box of SRC-1 (52). We hypothesized that the LxxIL motif of the C-terminus of NRIF3 contacts the co-activator binding site of the nuclear receptors, and the automatic docking procedure was carried out towards this site (71, 75, 76). Two critical features of the interaction between the LBDs of nuclear hormone receptors and their co-activators were used to build the models: 1) The "charge clamp", initially observed in the complex between SRC-1 and PPARγ (56), where a conserved glutamate and lysine at opposite ends of the hydrophobic cavity of the receptors contact the backbone of the co-activator's LxxLL box. This feature enabled the orientation of the NRIF3 helical peptide and, 2) The finding that the leucines of the LxxLL motif of SRC-1 are buried into the hydrophobic cavity of the receptor. This feature makes predictions of the side of the NRIF3 peptide which faces the receptor.

The co-activator peptides were assigned a helical secondary structure, the backbone $\phi$ and $\psi$ angles being −62 and −41 degrees, respectively. The $\omega$ angle was set to 180 degrees. Loose distance restraints were set between the "charge clamp" of the receptors (56) and $C^\alpha$ atoms of the peptide. The energy of the complex was minimized in the internal coordinate space using the modified ECEPP/3 potentials. The subset of the variables minimized with the ICM method (1, 71, 76), included the side-chains of the receptor, six positional variables of the helix and the side-chain torsion angles of the helix.

Binding energy calculation. The binding energy was calculated by the partitioning method as described elsewhere (64). Briefly, the binding energy function is partitioned into three terms: the surface (or hydrophobic) term, determined as the product of the solvent accessible surface by a surface tension of 30 cal/mol/Å$^2$, the electrostatic term, calculated by a boundary element algorithm, with a dielectric constant of 8, and the entropic term, which results from the decrease in conformational freedom of residue side-chains partially or completely buried upon complexation.

Results

Cloning of NRIF3 cDNA. To isolate potential co-activators mediating the transcriptional activation function of nuclear receptors, we employed a yeast two-hybrid screening strategy (29). A bait expressing a full length TRα fused to the C-terminus of the LexA DNA binding domain was used to screen a HeLa cell cDNA library cloned into pJG4-5 (29). Candidate clones that exhibited a thyroid hormone (T3)-dependent interaction with LexA-TRα were selected and further examined and sequenced. Four novel clones were identified and all were found to exhibit similar interaction with the ligand binding domain (LBD) of TRα as with full length receptor (data not shown). These clones were designated as NRIF1, 2, 3 and 4 (Nuclear receptor interacting factors). Not surprisingly, the LBD of TRb was also found to interact with these NRIFs in a T3-dependent manner (data not shown). Among these four isolated NRIFs, NRIF3 was a full length clone. As shown in FIG. 1, LexA alone (negative control) does not interact with NRIF3 (as indicated by the low β-galactosidase activity) and incubation with T3 has no effect. Similarly, no interaction was detected between the LexA-TR LBD and B42 alone with or without T3 (data not shown). The LexA-TR LBD also shows little interaction with NRIF3 in the absence of T3. However, incubation with T3 results in strong stimulation of the NRIF3-TR LBD interaction (FIG. 1). The extent of T3-dependent interaction between NRIF3 and LexA-TR LBD was similar to that of Trip1 (FIG. 1), one of the first thyroid hormone receptor interacting factors cloned using a two-hybrid screen (42).

Sequence analysis of NRIF3. Sequence analysis of the NRIF3 cDNA revealed a single open reading frame (ORF) encoding a polypeptide of 177 amino acids (FIG. 2). NRIF3 shares no homology with members of the SRC-1 and CBP/p300 families. The size of NRIF3 is in sharp contrast to the size of CBP/p300 (around 300 kd), or the SRC-1 family (around 160 kd). NRIF3 contains a putative nuclear localization signal (KRKK; (SEQ ID NO:5), as well as one copy of an LxxLL (SEQ ID NO:1) motif (amino acids 9–13) that was recently identified to be essential for the interaction of a number of putative co-activators with nuclear receptors (32).

A database search identified two highly-related homologs of NRIF3, which were previously designated as β3-endonexin short form and long form (67). The endonexin short form (EnS) was originally isolated from a two-hybrid screen intended to clone factors that interact with the cytoplasmic tail of integrin β3 (67). The long form (EnL) was then identified as an alternatively spliced product of the same gene. However, the long form does not bind to integrin β3 (67). Nucleotide sequence comparisons between cDNAs of NRIF3 and endonexin short or long forms indicate that NRIF3 is a third alternatively spliced product of the same gene (alignment not shown). The precise function(s) of the two endonexin proteins is currently under investigation.

Figure 3A:
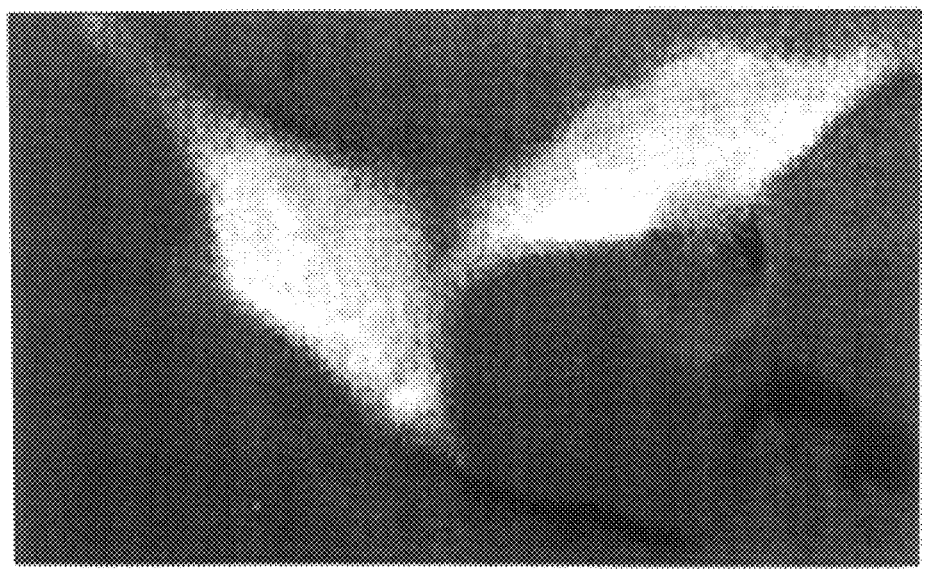
FIG. 3. NRIF3 is a nuclear protein. HeLa cells were transfected with a expression vector for GFP (left panel) or GFP-NRIF3 (right panel). The cellular location of the expressed proteins was visualized by fluorescence microscopy.
Figure 3B:
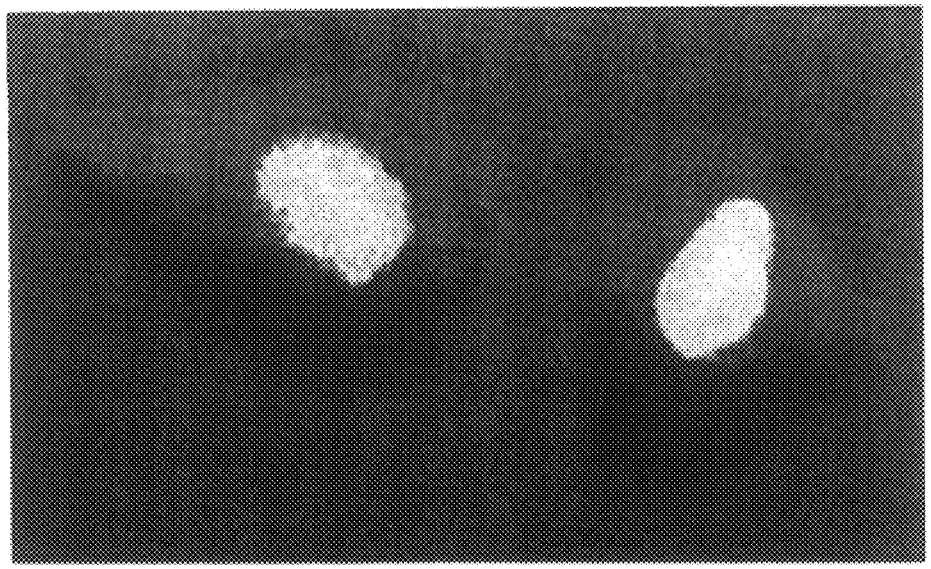

NRIF3 localizes to the cell nucleus. Although a putative nuclear localization signal was found in NRIF3, we considered it important to identify the subcellular location of the NRIF3 protein since extensive homology was found between NRIF3 and the two endonexins. The entire NRIF3 ORF was fused to the C-terminus of green fluorescent protein (GFP) (18). The resulting GFP-NRIF3 fusion protein was expressed in HeLa cells by transient transfection and the subcellular location of the fusion protein was visualized by fluorescence-microscopy. As shown in FIG. 3, the control GFP protein is distributed throughout the cell while GFP-NRIF3 is localized exclusively to the nucleus. This result suggests that NRIF3 is a nuclear protein, which is compatible with its putative role as a nuclear receptor co-activator.

Selective interaction of NRIF3 with liganded nuclear receptors in yeast. Although NRIF3 was originally cloned using full length TRα as the bait, we later identified that the region of the receptor responsible for NRIF3 binding is its LBD (see FIG. 1). A common feature among most of the known co-activators that show ligand-dependent interaction with nuclear receptors is the presence of the LxxLL (SEQ ID NO:1) motif(s) in their receptor interaction domains. The LxxLL motif appears to be involved in direct contact with a structurally-conserved surface in the ligand-bound LBDs of the receptors (23), which may provide the molecular basis for the broad spectrum of receptor binding by co-activators such as SRC-1 or GRIP1. Since a putative LxxLL motif is also present in NRIF3 (amino acids 9–13), we asked whether NRIF3 also interacts with the LBDs of other nuclear receptors.

The LBDs of several nuclear receptors were examined for interaction with NRIF3 in a yeast two hybrid assay. As shown in Table 1, NRIF3 does not interact with LexA alone (negative control) with (+) or without (−) ligand. LexA-TR and LexA-RXR show little (if any) interaction with NRIF3 in the absence of their cognate ligands. However, the presence of T3 (for TR) or 9-cis RA (for RXR) results in a strong stimulation of their interaction with NRIF3, as indicated by the induction of β-galactosidase activity (Table 1). Interestingly, when LexA-RAR or LexA-GR was used as the bait, no interaction was detected with NRIF3 in the presence or absence of their cognate ligands (Table 1). The finding that NRIF3 interacts with TR but not RAR was surprising in light of a recent study, which shows that TR and RAR functionally interact with the same LxxLL (SEQ ID NO:1) boxes (boxes 2 and 3) of SRC-1/NCoA-1 (52). As positive controls, we confirmed that both LexA-RAR and LexA-GR exhibited ligand-dependent interaction with other co-activators that are not receptor-specific (data not shown). Taken together, these results suggest that NRIF3 exhibits differential specificity in its interaction with different nuclear receptors.

TABLE 1

Interaction of NRIF 3 with Nuclear Receptors in Yeast

| Bait | Prey | β-galactosidase activity | | Fold Stimulation |
|---|---|---|---|---|
| | | Ligand − | Ligand + | |
| LexA | NRIF3-B42 | 2.3 | 1.9 | 0.8 |
| LexA-TR | NRIF3-B42 | 1.8 | 125 | 69 |
| LexA-RAR | NRIF3-B42 | 0.1 | 0.1 | 1 |
| LexA-RXR | NRIF3-B42 | 0.2 | 63 | 315 |
| LexA-GR | NRIF3-B42 | 0.8 | 0.6 | 0.8 |

The LacZ reporter activity was determined for yeast strains harboring the indicated bait and prey plasmids in the presence of (+) or absence (−) of cognate ligands as described in Materials and Methods. See text for detailed explanations.

Figure 4:
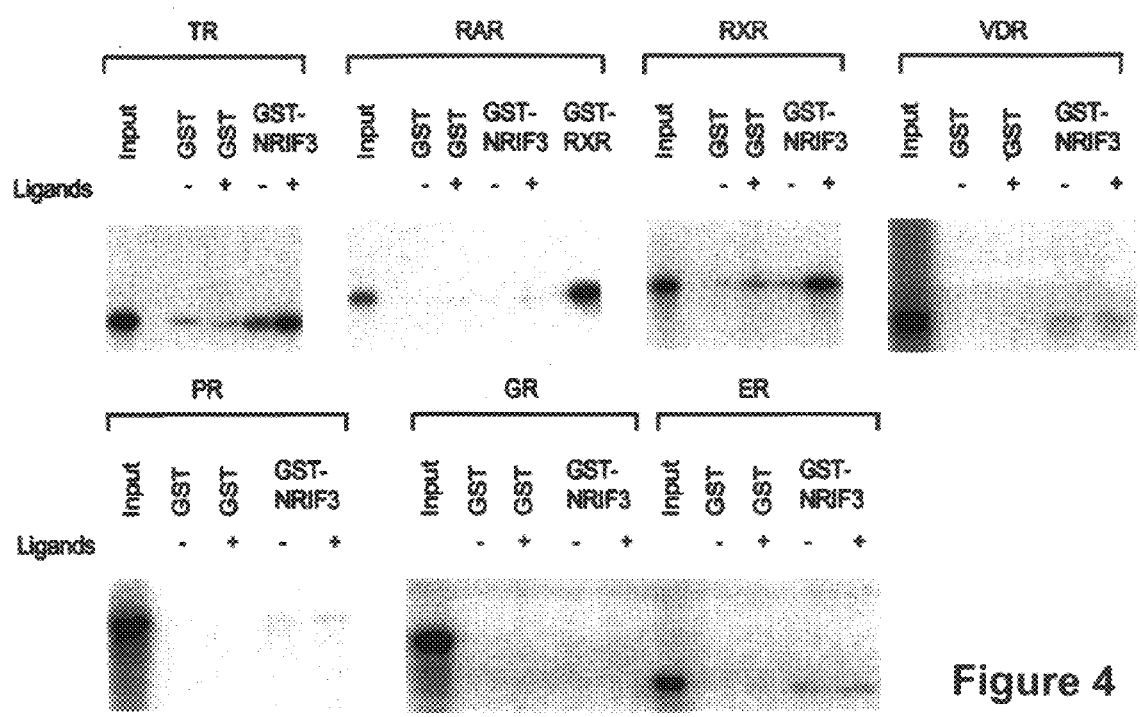
FIG. 4. Characterization of the NRIF3 interaction with nuclear receptors in vitro. $^{35}$S-labeled full length receptor (cTRα, hRARα, hRXRα, hVDR, hPR, hGR, or hER) was incubated with affinity purified GST control or GST-NRIF3 linked to glutathione-agarose beads. The binding was performed in the absence (−) or presence (+) of cognate ligands as described in Materials and Methods. After incubation and washing, the bound receptors were analyzed in 10% SDS-PAGE and detected by autoradiography. The input lane in each binding assay represents 5% of the total $^{35}$S-labeled receptor used in each incubation. GST-RXR was used as a positive control for RAR binding.

NRIF3 specifically binds to TR and RXR but not to other nuclear receptors in vitro. To further examine the interaction between NRIF3 and various nuclear receptors as well as to confirm the potential receptor specificity of NRIF3, in vitro GST binding assays were performed (30). $^{35}$S-labeled nuclear receptor, generated by in vitro transcription/translation, was incubated with purified GST-NRIF3 or the GST control bound to glutathione-agarose beads. All binding assays were carried out with (+) or without (−) the cognate ligand of the examined receptor. As shown in FIG. 4 (top left), TR and NRIF3 interact poorly in the absence of T3. Addition of T3 results in a strong increase in TR binding to GST-NRIF3, confirming that NRIF3 associates with TR in a T3-dependent manner. Using similar binding assays, we also studied the interaction of NRIP3 with six other nuclear receptors. Consistent with our findings from the yeast two-hybrid studies (Table 1), NRIF3 interacts with RXR in vitro in a ligand-dependent manner (FIG. 4), but shows little or no binding to other nuclear receptors (RAR, VDR, GR, PR, and ER) in the presence or absence of their cognate ligands (FIG. 4). Taken together, the results of the yeast two-hybrid (Table 1) and the in vitro binding (FIG. 4) assays suggest that NRIF3 possesses a distinct receptor specificity.

Figure 5B:
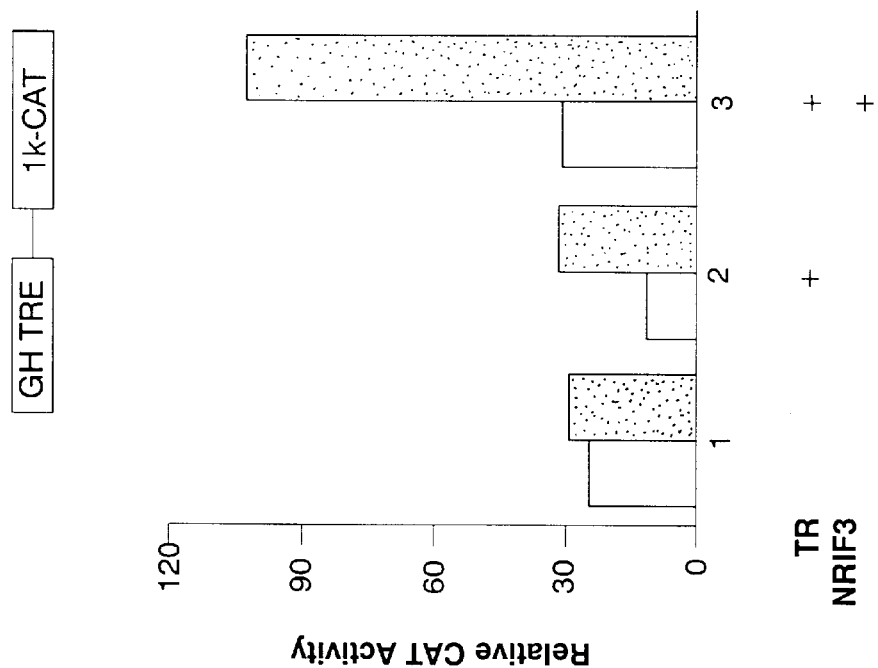
FIGS. 5A and 5B. NRIF3 enhances TR-mediated transactivation in vivo. HeLa cells were transfected with a vector expressing cTRα, and the IR-ΔMTV-CAT reporter (A) or the GH-TRE-tk-CAT reporter (B) in the presence (filled columns) or the absence (hatched columns) of 1 μM T3. The vector expressing NRIF3 or the empty control vector were co-transfected to examine the effect of NRIF3 on TR-mediated activation. In (A), the effect of CBP was compared to that of NRIF3.
Figure 5A:
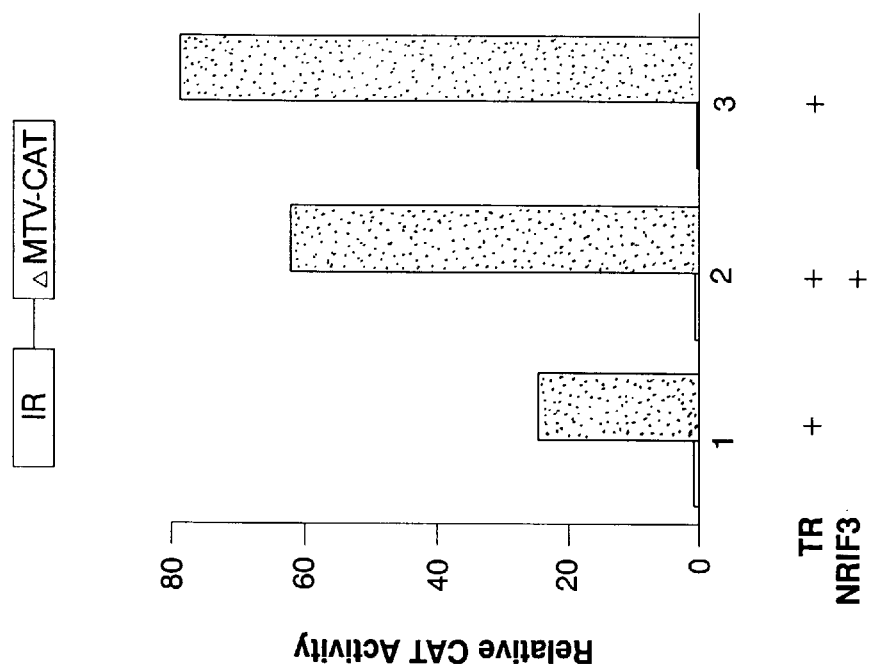

NRIF3 selectively potentiates TR- and RXR-mediated transactivation in vivo. To examine the potential role of NRIF3 in TR-mediated transactivation, transfection studies were carried out. HeLa cells, which lack endogenous TR (25), were transfected with a vector expressing TR, and a CAT reporter under the control of the AMTV basal promoter linked to an idealized inverted repeat (IR) (AGGTCATGACCT; (SEQ ID NO:9) TRE sequence (IR-ΔMTV-CAT) (25), along with either a control plasmid or a vector expressing NRIF3. As shown in FIG. 5A, NRIF3 significantly enhances TR-mediated activation of the CAT reporter (typically 2.5- to 3-fold). As a control, we also examined the effect of CBP, a reported co-activator for nuclear receptors (13, 37), and found that its expression results in a similar degree of enhancement as with NRIF3 (around 3-fold) (FIG. 5A).

We also examined another CAT reporter controlled by the Herpes virus thymidine kinase (tk) promoter linked to native rat growth hormone (GH) TRE sequences (5). NRIF3 was found to also enhance TR-mediated activation of this reporter (about 3.5-fold) (FIG. 5B). In addition, using similar transfection assays, we found that NRIF3 enhances TR-mediated activation of two other reporters, (IR)2-TATA-CAT and DR4-ΔMTV-CAT (data not shown). Therefore, NRIF3 potentiates TR-mediated transactivation in a variety of different TRE/promoter contexts. Taken together, the results of these transfection studies suggest that NRIF3 can function as a co-activator of TR.

Figure 6A:
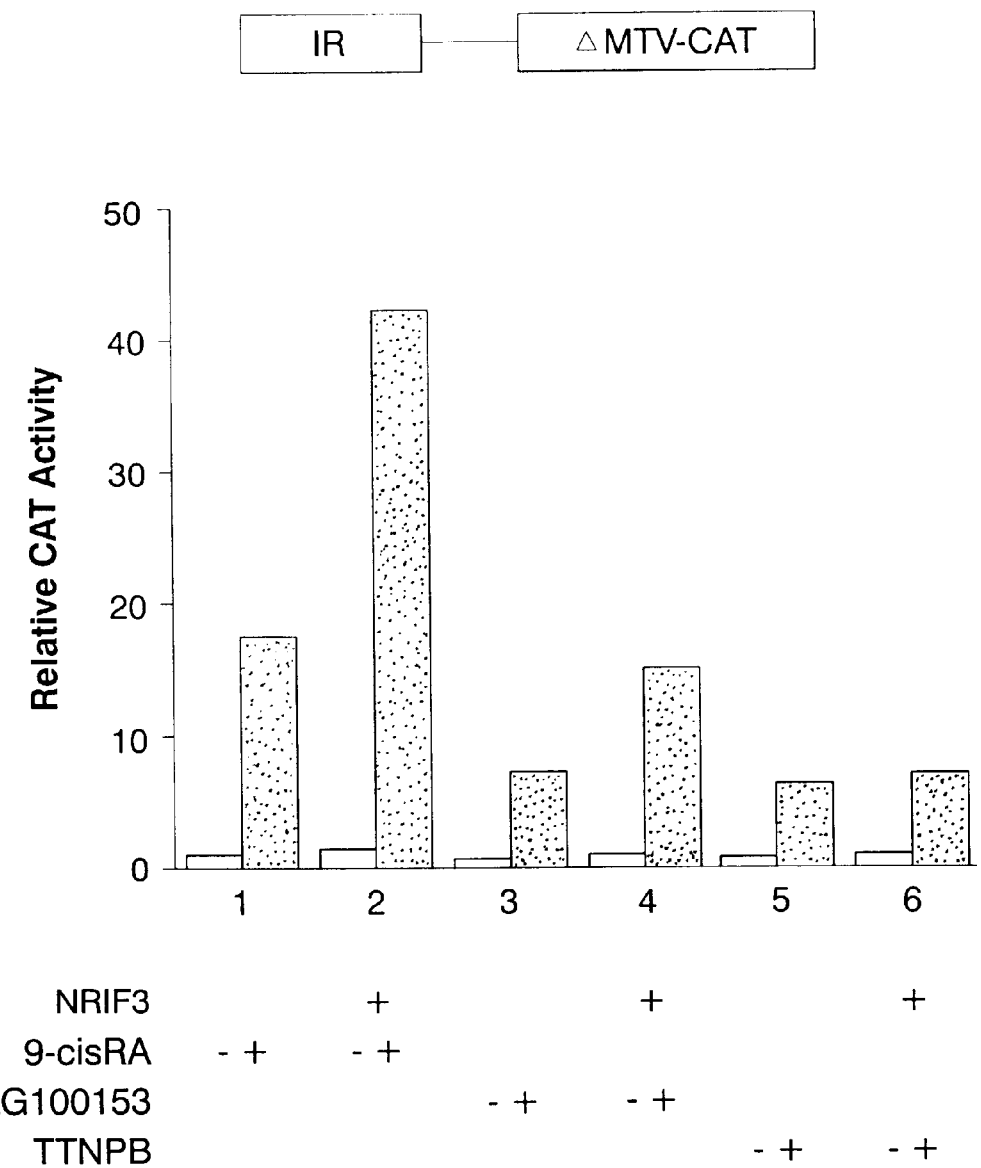
FIGS. 6A, 6B, and 6C. NRIF3 functions as a co-activator for RXR but not RAR. (A) NRIF3 potentiates the activity of endogenous RXR(s) but not RAR(s). HeLa cells were transfected with the IR-ΔMTV-CAT reporter (without any receptor expression vector) to examine the activation by endogenous retinoid receptors. The NRIF3 expression vector or the empty control vector were co-transfected to examine the effect of NRIF3 on the activity of endogenous RXR(s) or RAR(s). Relative CAT activity was determined in the presence (filled columns) or absence (hatched columns) of indicated ligands (1 μM). (B), (C) NRIF3 potentiates the activity of exogenously expressed RXR. A vector expressing hRXRα was co-transfected into HeLa cells with the IR-ΔMTV-CAT reporter (B) or the DR1-ΔMTV-CAT reporter (C), in the presence (filled columns) or absence (hatched columns) of indicated ligands (1 μM). The effect of NRIF3 on RXR-mediated transactivation was similarly examined as in (A).

To examine whether NRIF3 can also act as a co-activator for RXR, HeLa cells were transfected with the IR-ΔMTV-CAT reporter, whose IR sequence can also function as a strong response element for the RXR(s) and RAR(s) (25, 49, 61). HeLa cells express endogenous RXR(s) and RAR(s), as the activity of the IR-ΔMTV-CAT reporter is strongly stimulated by their cognate ligands, even without co-transfection of any receptor expression plasmid (FIG. 6A, panels 1, 3, and 5). Co-transfection of NRIF3 enhances the activation of this reporter by either 9-cis RA, or LG100153 (72), an RXR-specific ligand (FIG. 6A, panels 1 and 2; 3 and 4). In contrast, although the RAR-specific ligand TTNPB (68) also activates the IR-ΔMTV-CAT reporter, co-transfection of NRIF3 has no effect (FIG. 6A, panels 5 and 6). These results indicate that NRIF3 potentiates the activity of endogenous RXR(s) but not RAR(s), which is consistent with the distinct receptor specificity of NRIF3 revealed from the yeast two-hybrid assay (Table 1) and in vitro binding studies (FIG. 4).

Figure 6B:
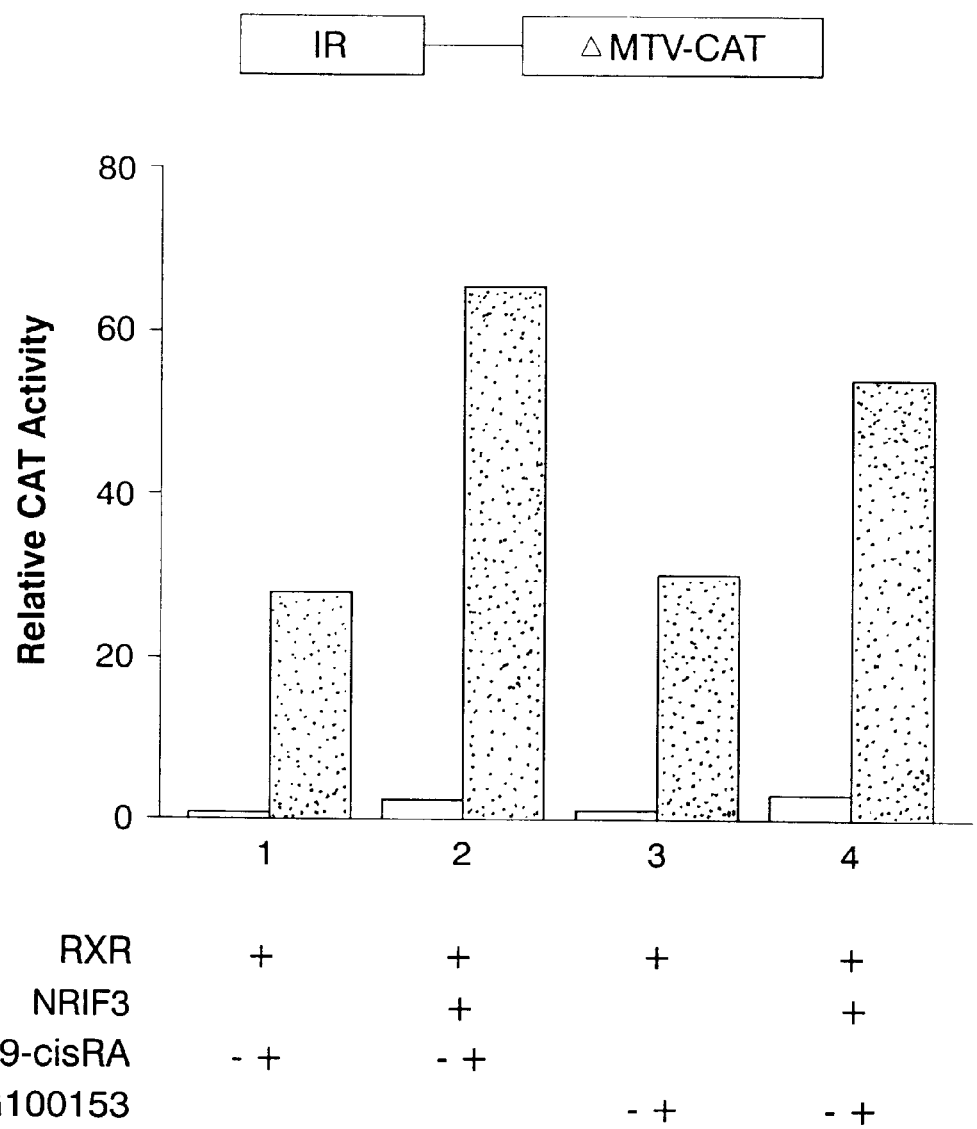
Figure 6C:
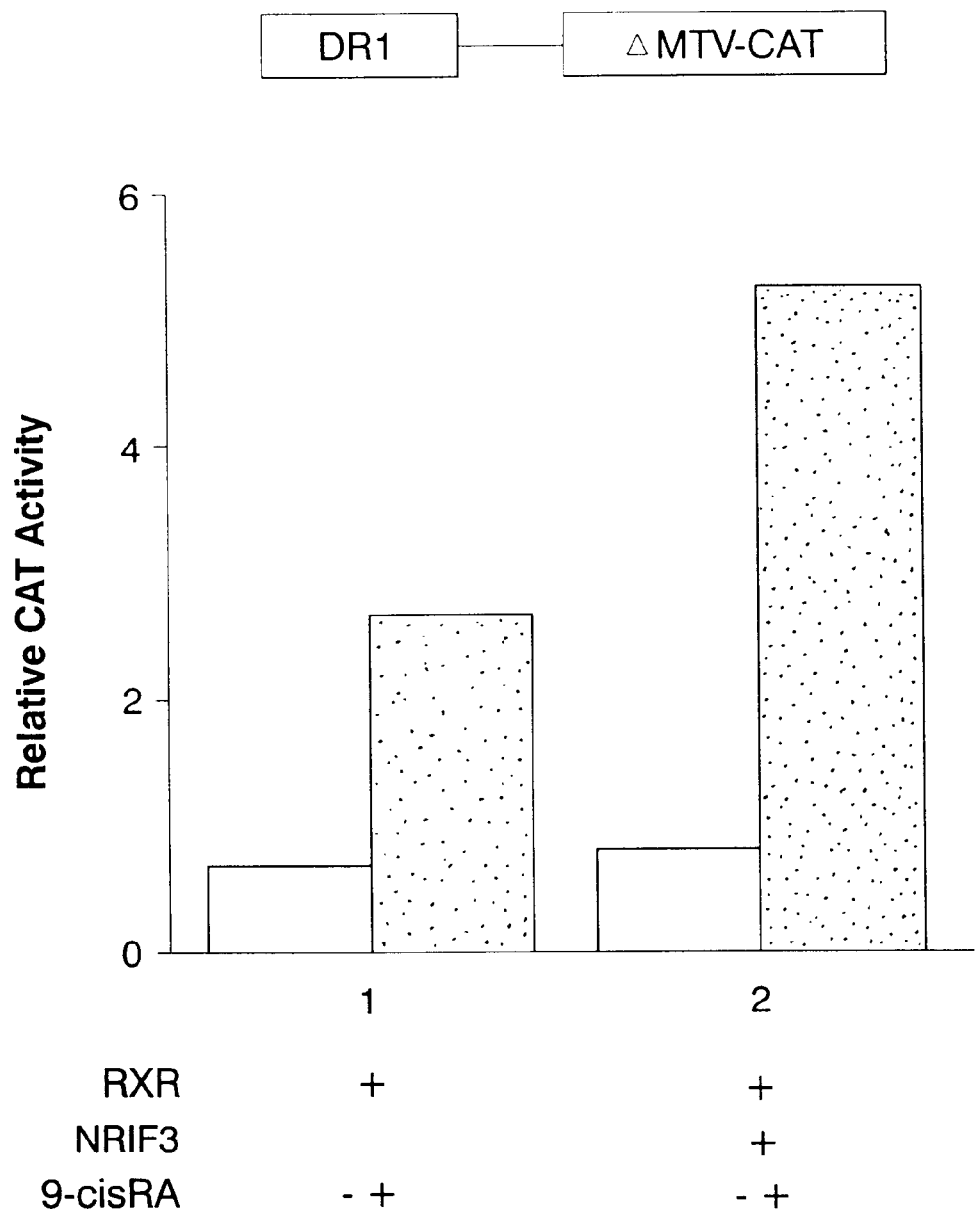

To further document that NRIF3 can function as a co-activator for RXR, a vector expressing exogenous RXR was co-transfected with IR-ΔMTV-CAT. Exogenous RXR expression enhances the activation of this CAT reporter by either 9-cis RA or LG100153 (comparing FIGS. 6B and 6A, panels 1 and 3). This RXR-mediated activation of reporter expression is further stimulated by NRIF3 (FIG. 6B). Finally, we also examined the activation of a DR1-ΔMTV-CAT reporter. This DR1 (AGGTCAnAGGTCA; SEQ ID NO:10) sequence is thought to be a specific response element for RXR (39, 51). In the sequence, n represents any nucleotide. Although we found that this DR1 is a weaker response element than the IR sequence, co-transfection of an RXR expression vector leads to ligand-induced activation of this DR1 reporter, which is also further enhanced by NRIF3 (FIG. 6C).

Figure 7A:
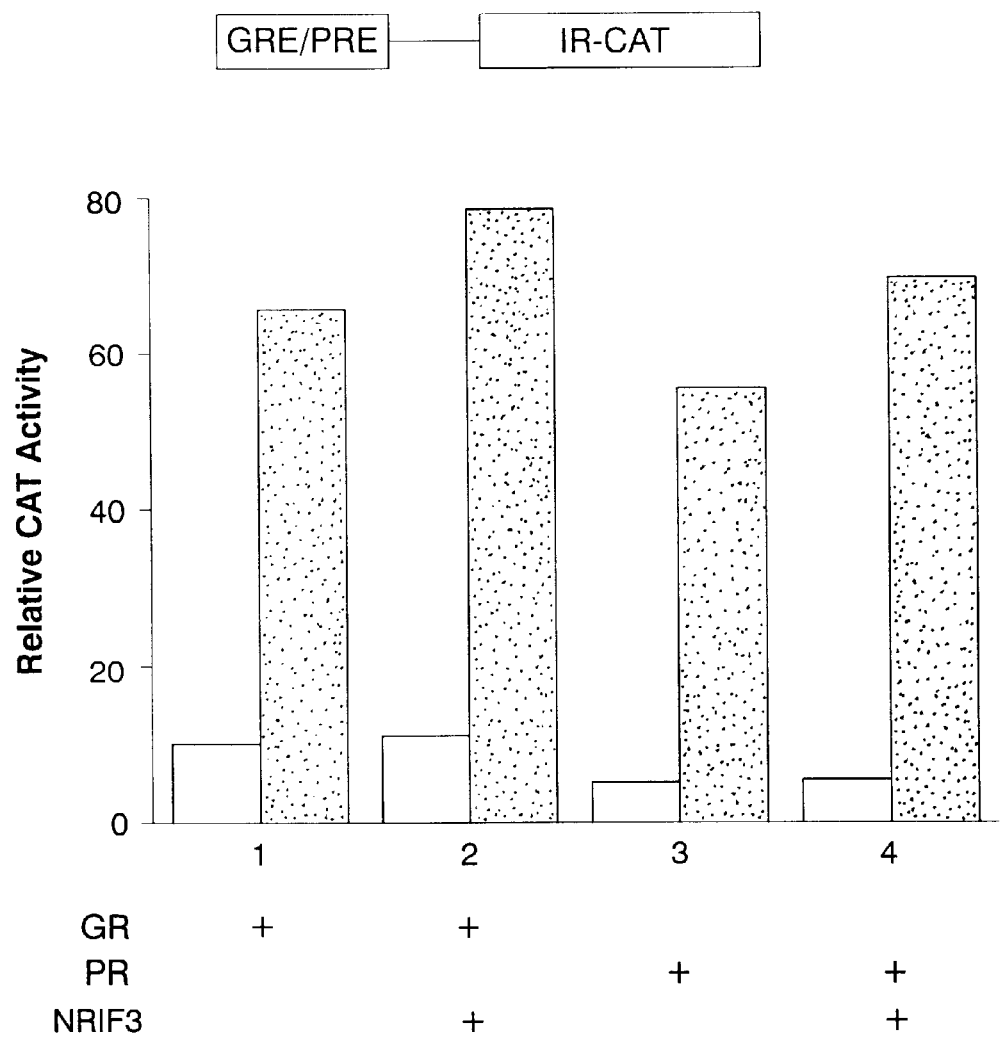
FIGS. 7A, 7B, and 7C. NRIF3 does not potentiate the activity of GR, PR, ER, or VDR. HeLa cells were transfected with the following CAT reporters and appropriate receptor expression vectors: GRE/PRE-tk-CAT and rGR or hPR (A), ERE-ΔMTV-CAT and hER (B), VDRE-ΔMTV-CAT and hVDR (C). Cells were incubated in the presence (filled columns) or absence (hatched columns) of 100 nM dexamethathone for GR, progesterone for PR, estradiol for ER, and 1,25-(OH)$_2$-VitD3 for VDR. Co-transfection of NRIF3 was found to have little effect on the activity of these receptors.
Figure 7B:
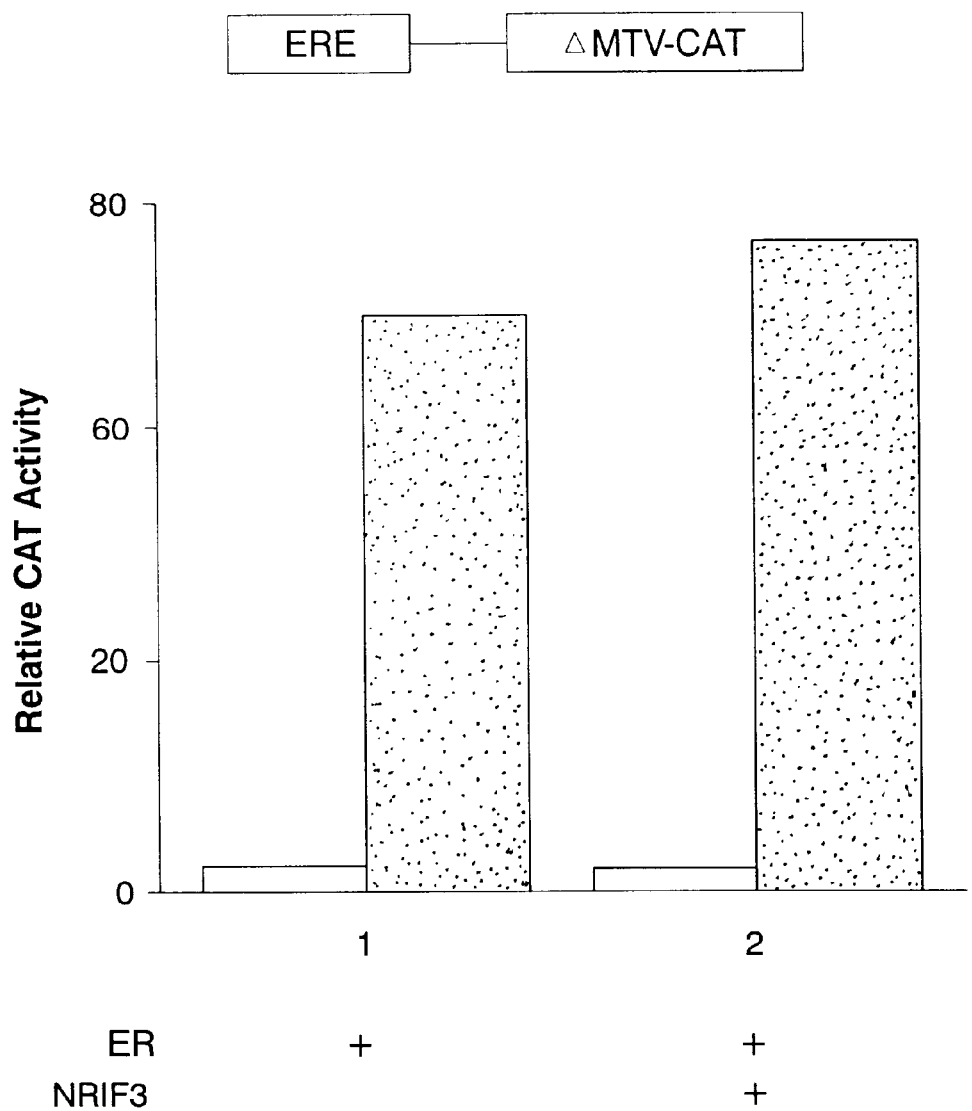
Figure 7C:
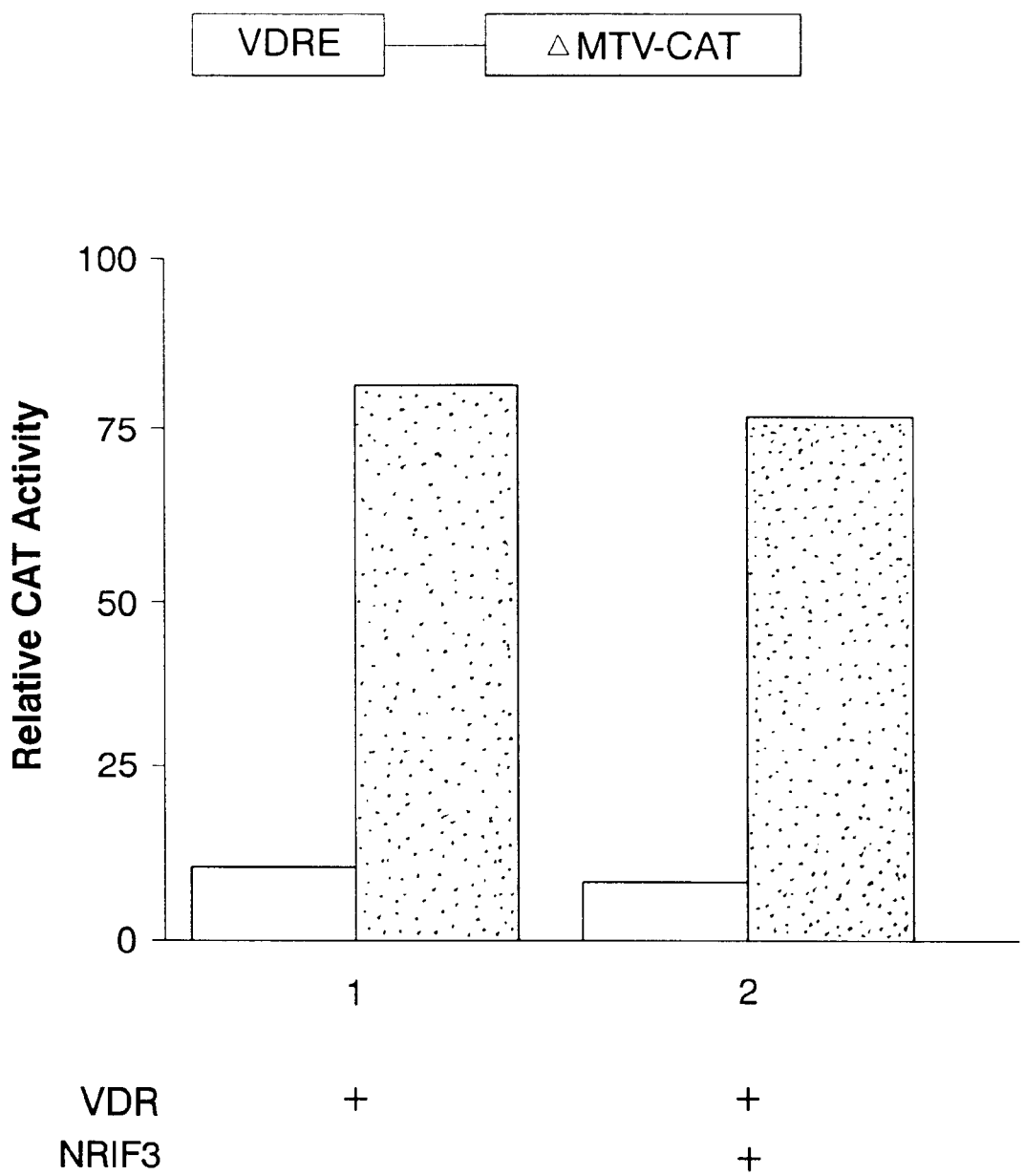

NRIF3 does not potentiate the activity of GR, PR, ER, and VDR in vivo. The selective co-activation of TR and RXR (but not RAR) by NRIF3 is consistent with its distinct binding specificity to these receptors. To further establish that NRIF3 acts as a receptor-specific co-activator, we next examined the effect of NRIF3 on the activity of four additional nuclear receptors, including GR, PR, ER, and VDR, by transfection studies. Hela cells were transfected with a GRE/PRE-tk-CAT reporter along with a vector expressing either GR or PR. As shown in FIG. 7A, cognate hormone treatment results in activation of the CAT reporter. However, expression of NRIF3 has little effect (FIG. 7A). Similar experiments were carried out using ER and ERE- ΔMTV-CAT, or VDR and VDRE-ΔMTV-CAT. As shown in FIG. 7B and 7C, NRIF3 was found to have little or no effect on the activity of these receptors as well. Taken together, the combined results of our transfection studies support the notion that NRIF3 is a co-activator with a unique receptor specificity.

A novel C-terminal domain in NRIF3 is essential for ligand-dependent interactions with TR and RXR. The LxxLL (SEQ ID NO:1) signature motif has been found to be present in the receptor interacting domain of many identified co-activators such as SRC-1/NCoA-1 and GRIP1/TIF-2 (32). The broad spectrum of receptor binding by co-activators such as SRC-1 suggests that the LxxLL-containing interacting domain may recognize a structurally-similar surface of these LBDs. Indeed, recent structural and functional studies revealed that the LxxLL motif and its nearby flanking amino acids are involved in direct contact with a hydrophobic cleft of the target surface presented by the ligand-bound LBDs of nuclear receptors (19, 23, 52, 56). The fact that NRIF3 also contains an LxxLL motif (amino acids 9–13, see FIG. 2 and FIG. 8A) and exhibits a distinct receptor specificity, raises the possibility that: 1), the motif and surrounding amino acids are involved in mediating receptor-specific interaction of NRIF3; or, 2) another region of NRIF3 (alone or in concert with the LxxLL motif region) plays an important role in mediating such interaction.

Figure 8A:
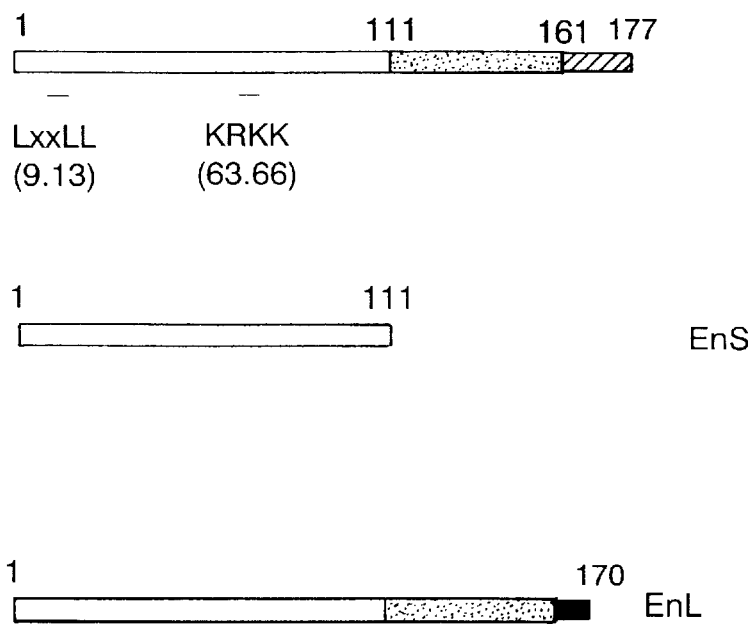
FIGS. 8A and 8B. The C-terminal domain of NRIF3 is essential for the interaction with liganded TR or RXR. (A) schematic comparison of NRIF3 with EnS and EnL. EnS is 100% identical to the first 111 amino acids of NRIF3 or EnL (open box). The region from amino acid 112 to 161 is 100% identical between NRIF3 and EnL (dotted box). NRIF3 and EnL differ in their C-terminus (16 amino acids in NRIF3, hatched box; and 9 amino acids in EnL, filled box). The positions of the LxxLL (SEQ ID NO:1) motif and a putative nuclear localization signal (KRKK; SEQ ID NO:5) are also indicated. (B) NRIF3 (N), EnS (S), or EnL (L) was examined for interaction with LexA-TR or LexA-RXR in a yeast two-hybrid assay as described in Materials and Methods. The assays were performed in the absence (hatched columns) or the presence (filled columns) of 1 μM T3 (for TR) or 9-cis RA (for RXR).
Figure 8B:
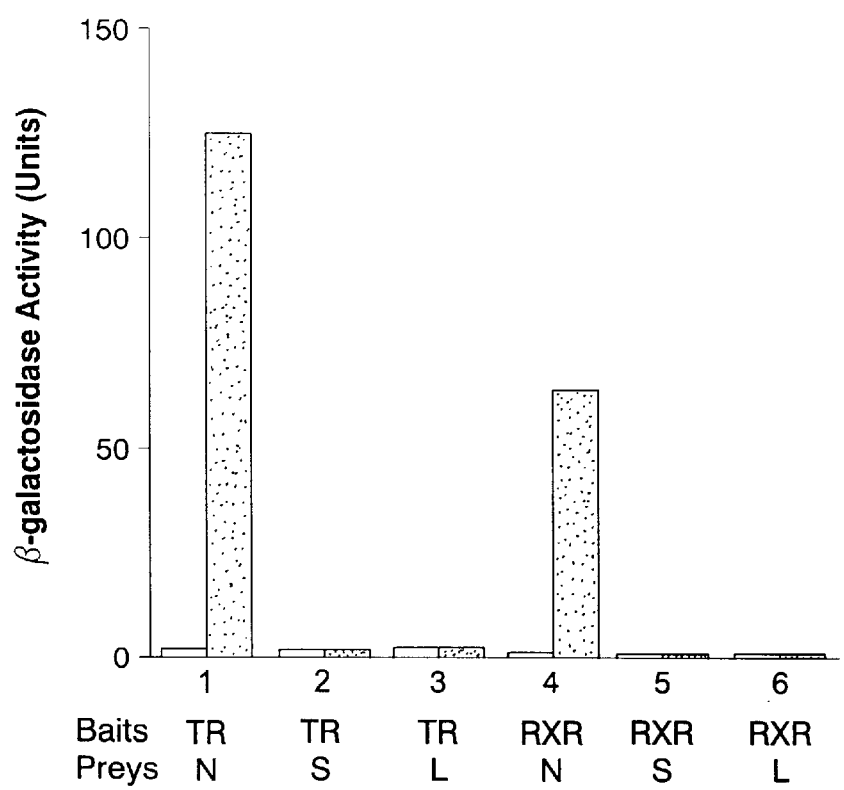

To explore these questions, we examined whether the endonexin short form (EnS) and endonexin long form (EnL), which contain the same LxxLL (SEQ ID NO:1) motif and flanking amino acids as NRIF3, can interact with nuclear receptors in a yeast two-hybrid assay (FIG. 8). EnS consists of 111 amino acids and is 100% identical to the first 111 residues of NRIF3, while the first 161 amino acids of EnL (170 amino acids) is also 100% identical to the same region in NRIF3 (see FIG. 2 legend and FIG. 8A). Thus, NRIF3 and EnL differ only in their C-terminus, with a unique region of 16 amino acids in NRIF3 or 9 residues in EnL (FIG. 8A). Interestingly, despite their extensive identity with NRIF3, the interaction with liganded TR or RXR is completely abolished in EnS and EnL (FIG. 8B). We also examined other nuclear receptors that do not interact with NRIF3 and found that they also do not interact with EnS or EnL (data not shown). These results indicate that the unique C-terminal domain in NRIF3 (residues 162–177) is essential for its specific interaction with liganded TR and RXR, while the N-terminal LxxLL motif (amino acids 9–13) and its flanking sequences are not sufficient to allow for detectable receptor interactions.

Figure 9:
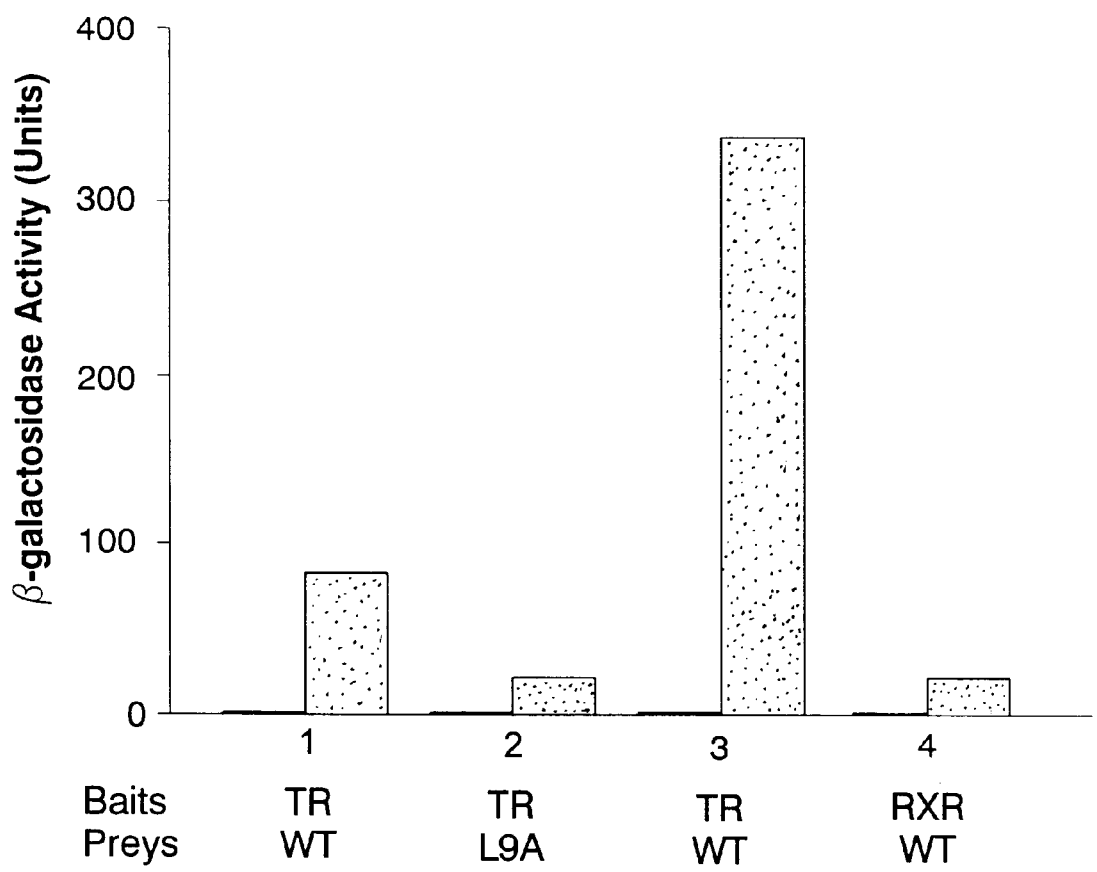
FIG. 9. The LxxLL (SEQ ID NO:1) motif of NRIF3 is required for optimum interaction with TR and RXR. Wild type NRIF3 (WT) or the L9A NRIF3 mutant (L9A) was examined for interaction with LexA-TR or LexA-RXR in a yeast two-hybrid assay as described in Materials and Methods. β-galactosidase activities were determined in the absence (filled columns) or presence (dotted columns) of cognate ligands (1 μM T3 for TR, 1 μM 9-cis RA for RXR).

Although found to be not sufficient for interaction, we examined whether the N-terminal LxxLL motif of NRIF3 contributes in the NRIF3/receptor interaction by mutating the first leucine of the LxxLL motif into alanine (L9A) by site-directed mutagenesis. Previous studies have shown that the three leucine residues are essential for an LxxLL module to interact with receptor LBDs, and the replacement of any of them with alanine would abolish the interaction (32). We examined the mutant NRIF3(L9A) for its interaction with TR and RXR in a yeast two-hybrid assay. As shown in FIG. 9, the L9A mutant is still capable of ligand-dependent interaction with TR and RXR (~25-fold induction by ligand). However, the introduced mutation reduces the interaction by about 4-fold (for TR) or 14-fold (for RXR). These results suggest that although the LxxLL motif is not absolutely essential for NRIF3 interaction with liganded receptors, it plays a role in allowing an optimum interaction to occur.

Figure 10:
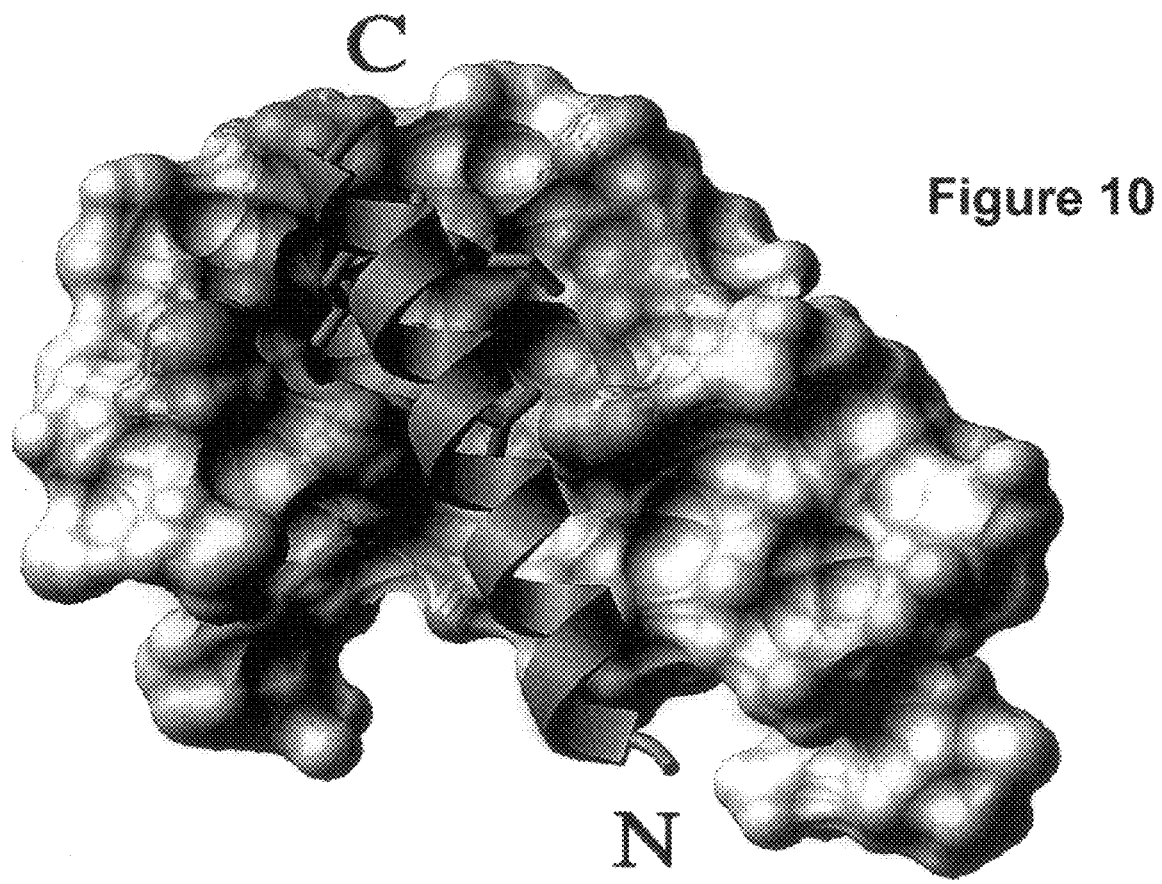
FIG. 10. A hypothetical model of interaction of the NRIF3 C-terminal domain is (NCD) and the liganded LBD. The docking of the C-terminal helix of NRIF3 which contains an LxxIL (SEQ ID NO:2) module to the ligand-bound LBDs was carried out as described in Materials and Methods. The NCD/TR LBD model is shown here as an example. The side chains of the two leucines (green) and one isoleucine (cyan) of the LxxIL core fit within a hydrophobic groove (salmon) on the surface of the liganded LBD. A similar modeling procedure was carried out using an LxxLL (SEQ ID NO:1) box of SRC-1 (result not shown). Putative binding energies (−21 kcal/mol for the NCD, and −18 kcal/mol for the LxxLL box of SRC-1) were calculated as described in Materials and Methods. See text for details.

Computer modeling suggests that the C-terminal domain of NRIF3 docks into the hydrophobic cleft of the liganded LBDs. Secondary structure analysis of the C-terminal domain of NRIF3 predicts the formation of an α-helix. Moreover, inspection of the putative C-terminal helix revealed an LxxIL (SEQ ID NO:2) motif (amino acids 172–176), which is reminiscent of the canonical LxxLL (SEQ ID NO:1). Although the ultimate elucidation of the molecular basis of the NRIF3-receptor interaction awaits future studies such as X-ray crystallography, the putative helix structure of the NRIF3 C-terminal domain and its LxxIL motif suggest that it may interact with the liganded LBDs in a similar fashion as to the receptor-interacting domains that employ the canonical LxxLL motif. To explore this possibility, we modeled the interaction of the C-terminus of NRIF3 with the liganded LBDs, using algorithms developed mainly by the laboratory of one of the authors (R. Abagyan and co-workers) (1, 63, 70, 74, 75). The background information and procedures used for constructing these models are described in Materials and Methods. The results of our modeling suggest that the NRIF3 C-terminal domain (referred as NCD) fits well into the hydrophobic cleft formed on the LBDs as a result of ligand binding. An example of such a model (NCD/TR LBD) is shown in FIG. 10. In this model, the two leucines and one isoleucine (green and cyan) of the LxxIL motif are predicted to be deeply buried into the central cavity of the hydrophobic groove formed by the liganded LBD of the receptor. We also calculated the putative binding energy for the modeled NCD/TR complex, using an improved partitioning binding energy function, with continuum representation of the electrostatics of the system (64). The calculated binding energy for the modeled NCD/TR complex is about −21 kca/mol. As a control, we carried out a similar modeling procedure using the second LxxLL box within the receptor interacting domain of SRC-1. This LxxLL box has been shown to be required for interaction with TR (52). Our calculated binding energy for this LxxLL box with liganded TR LBD is −18 kcal/mol, a value that is very close to the one calculated for the NRIF3 C-terminal domain. Altogether, our modeling and calculations suggest a mechanism in which the C-terminal domain of NRIF3 directly mediates interaction with liganded LBDs through an LxxIL motif.

Figure 11:
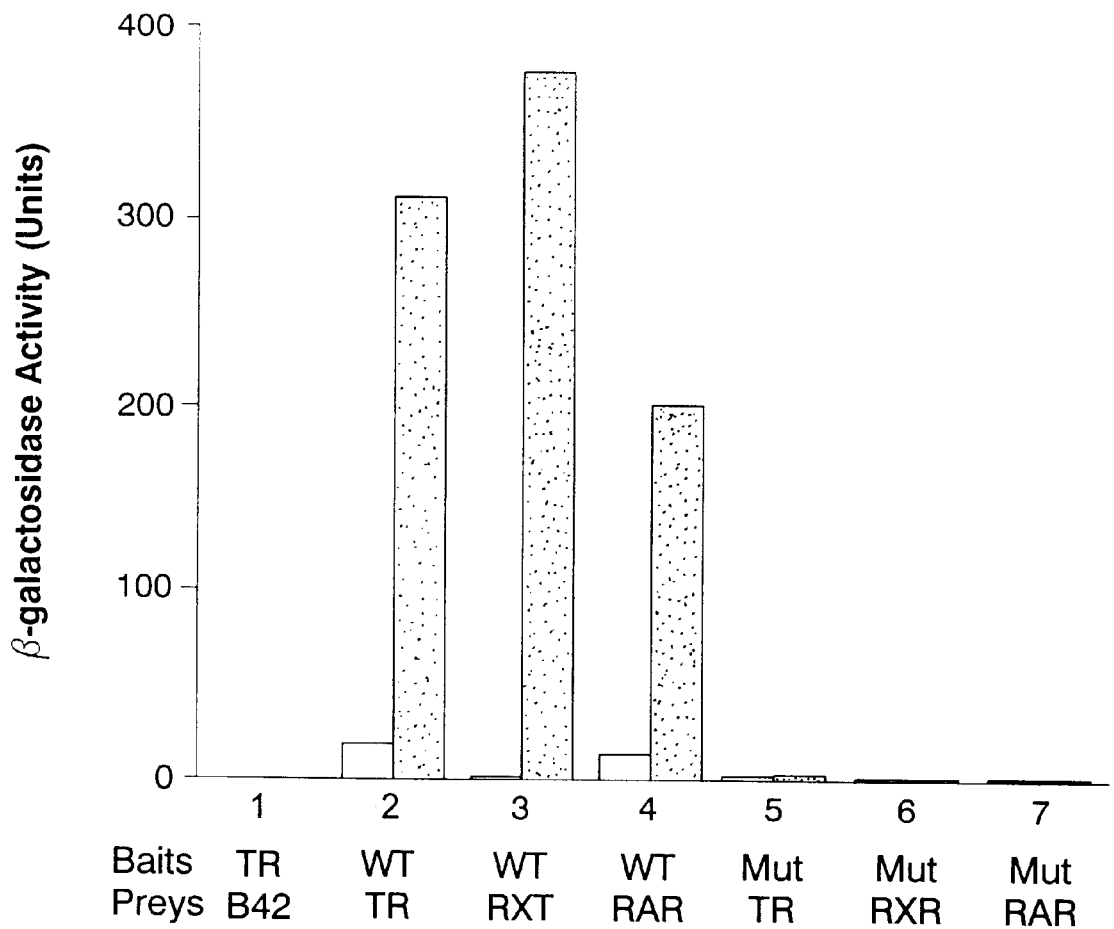
FIG. 11. Interaction of the NCD with the receptor LBDs and the role of the LxxIL motif. The wild type NCD (WT) or the NCD mutant form (Mut) in which the three core hydrophobic residues of the LxxIL (SEQ ID NO:2) motif (two leucines and one isoleucine) are changed into alanines, was examined for interaction the LBDs of TR, RXR, and RAR in a yeast two-hybrid assay as described in Materials and Methods. β-galactosidase activities were determined in the absence (empty columns) or presence (dotted columns) of cognate ligands. The prey expressing B42 alone was used as a negative control.

Functional interaction of the NRIF3 C-terminal domain with liganded LBDs and the essential role of its LxxIL motif. To explore the possibility suggested from our computer modeling, the C-terminal domain of NRIF3 (amino acids 162–177, referred as NCD) was fused to the LexA DNA binding domain and was examined for interaction with the receptor LBDs in a yeast two-hybrid assay. The LexA-NCD fusion protein alone does not activate the LacZ reporter in yeast (data not shown). As a negative control, we also found that LexA-NCD does not interact with the B-42 activation domain itself (FIG. 11), and LexA alone does not interact with the receptor LBDs (data not shown). However, when the LexA-NCD and the LBD of TR or RXR (fused with B-42) were used in the two-hybrid assay, a strong ligand-dpendent interaction was observed, as indicated by the induction of β-galactosidase activity by their cognate ligands (FIG. 11). These results suggest that the NRIF3 C-terminal domain can directly interact with the LBDs of TR and RXR in a ligand-dependent manner.

Since NRIF3 harbors a distinct receptor specificity in interacting only with TR and RXR but not other receptors (e.g. RAR), we next asked whether the NCD also harbors a receptor specificity. To our surprise, the NCD was found to interact efficiently with the LBD of RAR in a ligand-dependent manner (FIG. 11). Therefore, while our results clearly suggest that the NCD is an important surface for receptor interactions, as the NCD is found to be both essential for (FIG. 8) and sufficient to mediate such interactions (FIG. 11), it nevertheless does not appear to be (solely) responsible for the receptor specificity of NRIF3. It is possible that another region of the NRIF3 molecule may contribute to the observed receptor specificity of NRIF3, and/or, the specificity is determined by the overall three-dimensional structure of NRIF3.

Since our model predicts the importance of the LxxIL (SEQ ID NO:2) motif in the NCD-receptor interaction (FIG. 10), we tested this by changing the three core residues of the motif (two leucines and one isoleucine) into alanine. As expected, interaction with the LBDs is completely abolished in the resulting mutant NCD (FIG. 11), confirming that the LxxIL motif is essential for the interaction.

Discussion

Recent efforts in understanding receptor-mediated transcription have led to the identification of a number of co-activators for nuclear hormone receptors, which can be categorized into two main groups based on overall homology, the SRC-1 family (including SRC-1/NCoA-1, TIF2/GRIP1/NCoA-2, AIB1/p/CIP/ACTR/RAC3/TRAM-1) (2, 14, 34, 35, 37, 44, 58, 73, 74, 79), and the CBP/p300 family (13, 31, 37). Other putative co-activators (e.g. ARA70 and PGC-1) that do not belong to the SRC-1 or CBP/p300 families have also been identified (60, 85). In addition, p/CAF may also be involved in receptor action through its association with nuclear receptors as well as with other co-activators (11, 14, 38, 83). Among these known co-activators, CBP/p300, members of the SRC-1 group, and p/CAF all possess HAT activities (8, 14, 57, 69, 83).

In this study we report the identification of a novel nuclear protein (NRIF3) which exhibits specific ligand-dependent interactions with TR and RXR but not with RAR, VDR, GR, PR, and ER. Functional studies indicate that NRIF3 potentiates TR- and RXR-mediated transactivation in vivo while it exhibits little or no effect on the activity of other examined receptors. Therefore, NRIF3 represents a novel co-activator with a distinct receptor specificity and, thus, may shed light on clarifying the molecular mechanism(s) underlying receptor-specific regulation of gene expression.

A database search indicated that NRIF3 shares no homology with any known co-activators except for a single LxxLL (SEQ ID NO:1) motif. An unusual feature of NRIF3 is its relatively small size, which is in sharp contrast to SRC-1 or CBP/p300. A homology search identified two alternatively spliced isoforms of NRIF3 which were previously designated as β3-endonexin short and long forms (67). Preliminary studies with these two endonexins indicate that, like NRIF3, they also localize to the cell nucleus (S. Shattil, personnel communication; Li and Samuels, unpublished data). Interestingly, despite their extensive identities with NRIF3, both the endonexin short and long forms fail to exhibit interaction with liganded nuclear receptors (see FIG. 8). Consistent with this finding, we found that the endonexin short and long forms have little effect on receptor-mediated transcription in transfection studies (data not shown). Therefore, the precise roles of these two endonexins remain to be elucidated. We suggest two not mutually-excluding possibilities. First, since both the endonexin long and short forms appear to localize to the nucleus, it is possible that they may act as co-factors for other transcriptional regulators. Second, since the endonexin short form can interact with the cytoplasmic tail of β3-integrin (22, 67), it may function to communicate signals generated at the plasma membrane to the cell nucleus. An example of a protein which is involved in both cell adhesion and transcriptional regulation is β-catenin (82).

Previous study of the endonexins identified the presence of NRIF3-related mRNAs (by Northern blots) in a wide range of human tissues (67). Because NRIF3 and the endonexin long form contain almost identical nucleotide sequences and differ only by an alternative splice which results in the removal of a small exon in NRIF3, it is difficult to specifically identify NRIF3 mRNA by Northern blots. A search of the expressed sequence tag database indicates that NRIF3 as well as both the endonexin long and short form mRNAs are expressed. However, the precise determination of cell and tissue distribution of the individual NRIF3 and endonexin short and long forms will require the development of highly selective antibodies. Nevertheless, the wide expression pattern of NRIF3-related mRNAs is consistent with the role of NRIF3 as a co-activator of the TRs, which are also widely expressed (70), or the RXRs, which are ubiquitously expressed (48).

A key question concerning the action of nuclear hormone receptors is to elucidate the molecular events underlying the functional specificity of different receptors in regulating the expression of their target genes. Determinants of specificity include specific ligand binding, selective binding of the receptors to their cognate response elements, as well as specific expression pattern of different receptors. These determinants alone, however, are not always sufficient to explain the extent of specificity observed for members of the nuclear receptor family. For example, several members of the thyroid hormone/retinoid receptor subfamily may bind similarly to common DNA elements while target genes containing those elements are only selectively activated by certain receptors (20, 47). Therefore, it is likely that additional factors (determined by cell/promoter contexts) are involved in determining receptor functional specificity. In this respect, most known co-activators do not appear to be receptor-specific. For example, members of the SRC-1 family and CBP/p300 interact with and appear to be involved in the action of many nuclear receptors (13, 14, 34, 37). Two known co-activators that may be involved in receptor-specific functions are ARA70 and PGC-1. The androgen receptor co-activator ARA70 has been reported to potentiate the activity of AR more efficiently than for other nuclear receptors (85). However, whether ARA70 can associate with other receptors remains to be thoroughly examined. The expression of PGC-1 is mainly restricted to the brown fat tissue and is thought to be directly involved in the regulation of thermogenesis by PPARγ (60). Nevertheless, PGC-1 exhibits a relatively broad spectrum of binding to different nuclear receptors. Therefore, the identification of NRIF3 represents the first example of a co-activator with such a clearly-defined receptor. specificity.

The receptor-specificity. of NRIF3 raises an interesting question about its. molecular mechanism. Domain analysis suggests that the LxxLL (SEQ ID NO:1) motif (amino acids 9–13) and its flanking sequences in NRIF3 are not sufficient for interaction with liganded nuclear receptors. In fact, such interaction is completely abolished in the endonexin long form, an alternatively spliced product which has the same LxxLL motif and contains the first 161 amino acids (out of a total of 177 amino acids) of NRIF3. This result suggests that a putative domain consisting of the last 16 amino acids of NRIF3 (residues 162–177) is essential for its interaction with liganded receptors. Inspection of this C-terminal region of NRIF3 (NCD) indicates that it contains an LxxIL (SEQ ID NO:2) motif (amino acids 172–176) and secondary structure analysis predicts the formation of an α-helix. The predicted helix structure and the similarity of LxxIL to the canonical LxxLL raise the possibility that this LxxIL-containing region may play a direct role in NRIF3-receptor interactions.

Our modeling of the NCD-LBD interaction (FIG. 10) suggests that the same hydrophobic groove in the ligand-bound LBD, which has been shown by previous studies to be the binding site for co-activators such as SRC-1/NCoA-1 or GRIP1 (19, 23, 56), appears also to be a suitable site for the docking of the C-terminal helix of NRIF3. Thus, the utilization of the complementary pair of an α-helix (in the co-activator) and a hydrophobic groove (in the receptor) for interaction seems to be a general scheme that also applies to NRIF3. The binding energy estimated for the NCD and the TR LBD (−21 kcal/mol) is similar to the one calculated for the second LxxLL box of SRC-1/NCoA-1 and the TR LBD (−18 kcal/mol). To explore the mechanisms suggested by the modeling, we found that the NCD can directly mediate interaction with the LBDs in a ligand-dependent manner (FIG. 11). Moreover, the LxxIL motif contained in the NCD was found to be essential for such interactions (FIG. 11). In summary, the combination of computer modeling and domain/mutagenesis analysis clearly suggest that the NCD is an important surface that is directly involved in interaction with the LBDs of the receptors, where the LxxIL motif of the NCD mimics the function of a canonical LxxLL. The AF-2 helix (which is a critical constituent of the hydrophobic groove formed upon ligand binding) of the LBD has been shown to be important for interaction with LxxLL boxes of the co-activators (23). Interestingly, we have examined two TR AF-2 mutants (66) and found that in both cases, ligand-dependent interaction with NRIF3 was abolished (Li and Samuels, unpublished data).

However, the NCD alone does not appear to harbor the same specificity as NRIF3 (see FIG. 11). Thus, it seems likely that another part of the NRIF3 molecule may contribute to the observed specificity, and/or, the specificity is determined by the overall three dimensional structure of NRIF3. In this regard, the potential role of the N-terminal LxxLL (SEQ ID NO:1) motif is intriguing. Although the N-terminal LxxLL motif (amino acids 9–13) is insufficient alone to mediate an interaction with TR or RXR (see FIG. 8), it can influence the interaction of NRIF3 with these receptors, as the NRIF3 L9A mutant retains significant but nevertheless reduced association with liganded TR or RXR (see FIG. 9). Thus, NRIF3 appears to employ at least two regions in interacting with liganded TR or RXR, with the NCD playing an essential role and the N-terminal LxxLL motif playing a secondary role. A simplified explanation for these findings would be that the NCD provides a major surface for receptor binding, while the N-terminal LxxLL motif makes some minor contact with either the same receptor molecule, or more likely, with the other partner of a homodimer or heterodimer to further stabilize the NRIF3-receptor interaction. An example of a co-activator molecule employing two separate regions to interact with the two partners of a receptor dimer has been documented in the recently solved crystal structure of liganded PPARγ complexed with SRC-1/NCoA-1 (56). If NRIF3 indeed employs both its NCD and its N-terminal LxxLL motif in receptor interactions, the specificity may result from the intramolecular dialog between the two regions as well as the intermolecular dialog among NRIF3 and the receptors. However, it remains possible that the N-terminal LxxLL may only play a more indirect role and the overall three-dimensional structure of NRIF3 is responsible for its observed specificity.

Accumulating evidence suggests that the actions of transcriptional activating proteins are (usually) mediated by multi-protein complexes (59) and such a scheme is also likely for nuclear receptors. For example, biochemical evidence suggests that multi-protein complexes associate with liganded TR and VDR (24, 62, 86). Interestingly, many of the proteins identified in these studies are not known co-activators. While the study of known co-activators such as CBP/p300 and the SRC-1 family has suggested that histone acetylation may play an important role in receptor-mediated transactivation (8, 14, 57, 69), detailed elucidation of the transactivation mechanism(s) by these receptors awaits the identification and study of additional co-factors involved in the transactivation process.

Our results with NRIF3 suggest that transcriptional activation by nuclear receptors may employ receptor-specific co-activator(s) in addition to the generally-utilized co-activators such as CBP or SRC-1. Therefore, co-activators with NRIF3-like properties may contribute to the functional specificity of nuclear receptors in vivo. Based on our results with NRIF3 and previous studies of nuclear receptor action, we suggest a "combinatorial specificity model" where a co-activation complex is likely composed of two kinds of factors: "general factors" that interact with and are involved in the action of many nuclear receptors (such as CBP or SRC-1), and "specific factors" that exhibit receptor specificity (such as NRIF3). In addition to their interaction with the liganded receptor, co-activators may also communicate with each other within the co-activation complex through protein-protein interactions (e.g. CBP/p300 can interact with SRC-1/NCoA-1 or p/CIP) (37, 74, 84). An intriguing possibility is that the combinatorial actions of "specific factors" and other partners involved in the transactivation process facilitate the recruitment of specific co-activation complexes for different receptors (under different cell/promoter/HRE contexts), which would provide an important mechanistic layer for receptor functional specificity. An advantage of employing such a combinatorial strategy is that a broad array of diversity can be generated from a relatively small number of involved factors. Further study of NRIF3 with known and possibly other yet to be identified co-activators, as well as analysis of the interplay among these co-activators should provide important insights into the molecular mechanism(s) underlying the specificity of receptor-mediated regulation of target gene expression.

Example 2

Specific Antibodies Against NRIF3

Since alternative splicing of the NRIF3 gene generates multiple related mRNAs of similar sizes, it has been difficult to specifically identify the tissue/cell expression pattern of NRIF3 by Northern blot. To facilitate the detection of NRIF3, we have developed specific antibodies against NRIF3 protein. NRIF3 contains a unique C-terminal domain (amino acids 162–177, referred as NCD) that is not present in other alternatively-spliced products (known as endonexin short and long forms). Therefore, a polypeptide corresponding to the NCD was synthesized, linked to a carrier and used to immunize rabbits (Alpha Diagnostic International, San Antonio, Tex.). To examine the specificity of the polyclonal antibodies obtained from the rabbits, known amounts of purified recombinant NRIF3 as well as endonexin short and long forms were used for a Western blot analysis. The result of this analysis shows that less than 1 ng of the NRIF3 protein can be easily detected with our antibodies, while no cross-reaction was observed between the NRIF3 antibodies and the endonexin short or long forms even when more than a thousand fold of these two proteins were used in the assay.

Therefore, our NRIF3 antibodies appear to be both highly efficient and highly specific and should be an important tool in future studies involving NRIF3.

REFERENCES

1. Abagyan, R. A., M. M. Totrov, and D. A. Kuznetsov. 1994. ICM: a new method for structure modeling and design: Applications to docking and structure prediction from the distorted native conformation. J. Comp. Chem. 15:488–506.
2. Anzick, S. L., J. Kononen, R. L. Walker, D. O. Azorsa, M. M. Tanner, X. Y. Guan, G. Sauter, O. P. Kallioniemi, J. M. Trent, and P. S. Meltzer. 1997. AIB1, a steroid receptor coactivator amplified in breast and ovarian cancer. Science 277:965–968.
3. Arany, Z., D. Newsome, E. Oldread, D. M. Livingston, and R. Eckner. 1995. A family of transcriptional adaptor proteins targeted by the E1A oncoprotein. Nature 374:81–84.
4. Arias, J., A. S. Alberts, P. Brindle, F. X. Claret, T. Smeal, M. Karin, J. Feramisco, and M. Montminy. 1994. Activation of cAMP and mitogen responsive genes relies on a common nuclear factor. Nature 370:226–229.
5. Au-Fliegner, M., E. Helmer, J. Casanova, B. M. Raaka, and H. H. Samuels. 1993. The conserved ninth C-terminal heptad in thyroid hormone and retinoic acid receptors mediates diverse responses by affecting heterodimer but not homodimer formation. Mol. Cell. Biol. 13:5725–5737.
6. Baniahmad, A., X. Leng, T. P. Burris, S. Y. Tsai, M.-J. Tsai, and B. W. O'Malley. 1995. The τ4 activation domain of the thyroid hormone receptor is required for release of a putative corepressor(s) necessary for transcriptional silencing. Mol. Cell. Biol. 15:76–86.
7. Bannister, A. J., and T. Kouzarides. 1995. CBP-induced stimulation of c-Fos activity is abrogated by E1A. EMBO J. 14:4758–4762.
8. Bannister, A. J., and T. Kouzarides. 1996. The CBP co-activator is a histone acetyltransferase. Nature 384:641–643.
9. Barettino, D., M. d. M. V. Ruiz, and H. G. Stunnenberg. 1994. Characterization of the ligand-dependent transactivation domain of thyroid hormone receptor. EMBO J. 13:3039–3049.
10. Bhattacharya, S., R. Eckner, S. Grossman, E. Oldread, Z. Arany, A. D'Andrea, and D. M. Livingston. 1996. Cooperation of Stat2 and p300/CBP in signalling induced by interferon-alpha. Nature 383:344–347.
11. Blanco, J. C. G., S. Minucci, J. Lu, X. J. Yang, K. K. Walker, H. Chen, R. M. Evans, V. Nakatani, and K. Ozato. 1998. The histone acetylase PCAF is a nuclear receptor coactivator. Genes Dev. 12:1638–1651.
12. Casanova, J., E. Helmer, S. Selmi-Ruby, J.-S. Qi, M. Au-Fliegner, V. Desai-Yajnik, N. Koudinova, F. Yarm, B. M. Raaka, and H. H. Samuels. 1994. Functional evidence for ligand-dependent dissociation of thyroid hormone and retinoic acid receptors from an inhibitory cellular factor. Mol. Cell. Biol. 14:5756–5765.
13. Chakravarti, D., V. J. LaMorte, M. C. Nelson, T. Nakajima, I. G. Schulman, H. Juguilon, M. Montminy, and R. M. Evans. 1996. Role of CBP/P300 in nuclear receptor signalling. Nature 383:99–103.
14. Chen, H., R. J. Lin, R. L. Schiltz, D. Chakravarti, A. Nash, L. Nagy, M. L. Privalsky, Y. Nakatani, and R. M. Evans. 1997. Nuclear receptor coactivator ACTR is a novel histone acetyltransferase and forms a multimeric activation complex with P/CAF and CBP/p300. Cell 90:569–580.
15. Chen, J. D., and R. M. Evans. 1995. A transcriptional co-repressor that interacts with nuclear hormone receptors. Nature 377:454–457.
16. Chrivia, J. C., R. P. Kwok, N. Lamb, M. Hagiwara, M. R. Montminy, and R. H. Goodman. 1993. Phosphorylated CREB binds specifically to the nuclear protein CBP. Nature 365:855–859.
17. Conneely, O. M., W. P. Sullivan, D. O. Toft, M. Birnbaumer, R. G. Cook, B. L. Maxwell, T. Zaraucko-Schulz, G. L. Greene, W. T. Schraeder, and B. W. O'Malley. 1986. Molecular cloning of the chicken progesterone receptor. Science 233:767–770.
18. Cormack, B. P., R. H. Valdivia, and S. Falkow. 1996. FACS-optimized mutants of the green fluorescent protein (GFP). Gene 173:33–38.
19. Darimont, B. D., R. L. Wagner, J. W. Apriletti, M. R. Stallcup, P. J. Kushner, D. Baxter, R. J. Fletterick, and K. R. Yamamoto. 1998. Structure and specificity of nuclear receptor-coactivator interactions. Genes Dev. 12:3343–3356.
20. Desai-Yajnik, V., and H. H. Samuels. 1993. The NF-κB and Sp1 DNA motifs of the human immunodeficiency virus type 1 long terminal repeat function as novel thyroid hormone response elements. Mol. Cell. Biol. 13:5057–5069.
21. Durand, B., M. Saunders, C. Gausdon, B. Roy, R. Losson, and P. Chambon. 1994. Activation function 2 (AF-2) of retinoic acid receptor and 9-cis retinoic acid receptor: presence of a conserved autonomous constitutive activating domain and influence of the nature of the response element on AF-2 activity. EMBO 13:5370–5382.
22. Eigenthaler, M., L. Hofferer, S. J. Shattil, and M. H. Ginsberg. 1997. A conserved sequence motif in the integrin β3 cytoplasmic domain is required for its specific interaction with β3-endonexin. J. Biol. Chem. 272:7693–7698.
23. Feng, W., R. C. Ribeiro, R. L. Wagner, H. Nguyen, J. W. Apriletti, R. J. Fletterick, J. D. Baxter, P. J. Kushner, and B. L. West. 1998. Hormone-dependent coactivator binding to a hydrophobic cleft on nuclear receptors. Science 280:1747–1749.
24. Fondell, J. D., H. Ge, and R. G. Roeder. 1996. Ligand induction of a transcriptionally active thyroid hormone receptor coactivator complex. Proc. Natl. Acad. Sci. USA 93:8329–8333.
25. Forman, B. M., J. Casanova, B. M. Raaka, J. Ghysdael, and H. H. Samuels. 1992. Half-site spacing and orientation determines whether thyroid hormone and retinoic acid receptors and related factors bind to DNA response elements as monomers, homodimers, or heterodimers. Mol. Endocrinol. 6:429–442.
26. Giguere, V., E. S. Ong, P. Segui, and R. M. Evans. 1987. Identification of a receptor for the morphogen retinoic acid. Nature 330:624–629.
27. Glass, C. K., D. W. Rose, and M. G. Rosenfeld. 1997. Nuclear receptor coactivators. Curr. Opin. Cell Biol. 9:222–232.
28. Gu, W., X. L. Shi, and R. G. Roeder. 1997. Synergistic activation of transcription by CBP and p53. Nature 387:819–823.
29. Gyuris, J., E. Golemis, H. Chertkov, and R. Brent. 1993. Cdi1, a human G1 and S phase protein phosphatase that associates with Cdk2. Cell 75:791–803.
30. Hadzic, E., V. Desai-Yajnik, E. Helmer, S. Guo, S. Wu, N. Koudinova, J. Casanova, B. M. Raaka, and H. H. Samuels. 1995. A 10-amino-acid sequence in the N-terminal A/B domain of thyroid hormone receptor α is essential for transcriptional activation and interaction with the general transcription factor TFIIB. Mol. Cell. Biol. 15:4507–4517.
31. Hanstein, B., R. Eckner, J. DiRenzo, S. Halachmi, H. Liu, B. Searcy, R. Kurokawa, and M. Brown. 1996. p300 is a component of an estrogen receptor coactivator complex. Proc. Natl. Acad. Sci. USA 93:11540–11545.
32. Heery, D. M., E. Kalkhoven, S. Hoare, and M. G. Parker. 1997. A signature motif in transcriptional co-activators mediates binding to nuclear receptors. Nature 387:733–736.
33. Heinzel, T., R. M. Lavinsky, T. M. Mullen, M. Soderstrom, C. D. Laherty, J. Torchia, W. M. Yang, G. Brard, S. D. Ngo, J. R. Davie, E. Seto, R. N. Eisenman, D. W. Rose, C. K. Glass, and M. G. Rosenfeld. 1997. A complex containing N-CoR, mSin3 and histone deacetylase mediates transcriptional repression. Nature 387:43–48.
34. Hong, H., K. Kohli, M. Garabedian, and M. R. Stallcup. 1997. GRIP1, a transcriptional coactivator for the AF-2 transactivation domain of steroid, thyroid, retinoid, and vitamin D receptors. Mol. Cell. Biol. 17:2735–2744.
35. Hong, H., K. Kohli, A. Trivedi, D. L. Johnson, and M. R. Stallcup. 1996. GRIP1, a novel mouse protein that serves as a transcriptional coactivator in yeast for the hormone binding domains of steroid receptors. Proc. Natl. Acad. Sci. USA 93:4948–4952.
36. Horlein, A. J., A. M. Naar, T. Heinzel, J. Torchia, B. Gloss, R. Kurokawa, A. Ryan, Y. Kamil, M. Soderstrom, C. K. Glass, and M. G. Rosenfeld. 1995. Ligand-independent repression by the thyroid hormone receptor mediated by a nuclear receptor co-repressor. Nature 377:397–404.
37. Kamei, Y., L. Xu, T. Heinzel, J. Torchia, R. Kurokawa, B. Gloss, S.-C. Lin, R. A. Heyman, D. W. Rose, C. K. Glass, and M. G. Rosenfeld. 1996. A CBP integrator complex mediates transcriptional activation and AP-1 inhibition by nuclear receptors. Cell 85:403–414.
38. Korzus, E., J. Torchia, D. W. Rose, L. Xu, R. Kurokawa, E. M. McInerney, T. M. Mullen, C. K. Glass, and M. G. Rosenfeld. 1998. Transcription factor-specific requirements for coactivators and their acetyltransferase functions. Science 279:703–25 707.
39. Kurokawa, R., J. DiRenzo, M. Boehm, J. Sugarman, B. Gloss, M. G. Rosenfeld, R. A. Heyman, and C. K. Glass. 1994. Regulation of retinoid signalling by receptor polarity and allosteric control of ligand binding. Nature 371:528–531.
40. Kwok, R. P., J. R. Lundblad, J. C. Chrivia, J. P. Richards, H. P. Bachinger, R. G. Brennan, S. G. Roberts, M. R. Green, and R. H. Goodman. 1994. Nuclear protein CBP is a coactivator for the transcription factor CREB. Nature 370:223–226.
41. Lanz, R. B., N. J. McKenna, S. A. Onate, U. Albrecht, J. Wong, S. Y. Tsai, M. J. Tsai, and B. W. O'Malley. 1999. A steroid receptor coactivator, SRA, functions as an RNA and is present in an SRC-1 complex. Cell 97:17–27.
42. Lee, J. W., H.-S. Choi, J. Gyuris, R. Brent, and D. D. Moore. 1995. Two classes of proteins dependent on either the presence or absence of thyroid hormone for interaction with the thyroid hormone receptor. Mol. Endocrinol. 9:243–254.
43. Leng, X., J. Blanco, S. Y. Tsai, K. Ozato, B. W. O'Malley, and M.-J. Tsai. 1995. Mouse retinoid X receptor contains a separable ligand-binding and transactivation domain in its E region. Mol. Cell. Biol. 15:255–263.
44. Li, H., P. J. Gomes, and J. D. Chen. 1997. RAC3, a steroid/nuclear receptor-associated coactivator that is related to SRC-1 and TIF2. Proc. Natl. Acad. Sci. USA 94:8479–8484.
45. Lill, N. L., S. R. Grossman, D. Ginsberg, J. DeCaprio, and D. M. Livingston. 1997. Binding and modulation of p53 by p300/CBP coactivators. Nature 387:823–827.
46. Lundblad, J. R., R. P. Kwok, M. E. Laurance, M. L. Harter, and R. H. Goodman. 1995. Adenoviral E1A-associated protein p300 as a functional homologue of the transcriptional co-activator CBP. Nature 374:85–88.
47. MacDonald, P. N., D. R. Dowd, S. Nakajima, M. A. Galligan, M. C. Reeder, C. A. Haussler, K. Ozato, and M. R. Haussler. 1993. Retinoid X receptors stimulate and 9-cis retinoic acid inhibits 1,25-dihydroxyvitamin $D_3$-activated expression in the rat osteocalcin gene. Mol. Cell. Biol. 13:5907–5917.
48. Mangelsdorf, D. J., U. Borgmeyer, R. A. Heyman, J. Y. Zhou, E. S. Ong, A. E. Oro, A. Kakizuka, and R. M. Evans. 1992. Characterization of three RXR genes that mediate the action of 9-cis retinoic acid. Genes Dev. 6:329–344.
49. Mangelsdorf, D. J., and R. M. Evans. 1995. The RXR heterodimers and orphan receptors. Cell 83:841–850.
50. Mangelsdorf, D. J., E. S. Ong, J. A. Dyck, and R. M. Evans. 1990. Nuclear receptor that identifies a novel retinoic acid response pathway. Nature 345:224–229.
51. Mangelsdorf, D. J., C. Thummel, M. Beato, P. Herrlich, G. Schutz, K. Umesono, B. Blumberg, P. Kastner, M. Mark, P. Chambon, and R. M. Evans. 1995. The nuclear receptor superfamily: the second decade. Cell 83:835–839.
52. McInerney, E. M., D. W. Rose, S. E. Flynn, S. Westin, T. M. Mullen, A. Krones, J. Inostroza, J. Torchia, R. T. Nolte, N. Assa-Munt, M. V. Milburn, C. K. Glass, and M. G. Rosenfeld. 1998. Determinants of coactivator LXXLL motif specificity in nuclear receptor transcriptional activation. Genes Dev. 12:3357–3368.
53. Miesfeld, R., S. Rusconi, P. J. Godowski, B. A. Maler, S. Okret, A.-C. Wikstrom, J.-A. Gustafsson, and K. R. Yamamoto. 1986. Genetic complementation of a glucocorticoid receptor deficiency by expression of cloned receptor cDNA. Cell 46:389–399.
54. Nagpal, S., S. Friant, H. Nakshatri, and P. Chambon. 1993. RARs and RXRs: evidence for two autonomous transactivation functions (AF-1 and AF-2) and heterodimerization in vivo. EMBO J. 12:2349–2360.
55. Nagy, L., H. V. Kao, D. Chakravarti, R. J. Lin, C. A. Hassig, D. E. Ayer, S. L. Schreiber, and R. M. Evans. 1997. Nuclear receptor repression mediated by a complex containing SMRT, mSin3A, and histone deacetylase. Cell 89:373–380.
56. Nolte, R. T., G. B. Wisely, S. Westin, J. E. Cobb, M. H. Lambert, R. Kurokawa, M. G. Rosenfeld, T. M. Willson, C. K. Glass, and M. V. Milburn. 1998. Ligand binding and co-activator assembly of the peroxisome proliferator-activated receptors. Nature 395:137–143.
57. Ogryzko, V. V., R. L. Schiltz, V. Russanova, B. H. Howard, and Y. Nakatani. 1996. The transcriptional coactivators p300 and CBP are histone acetyltransferases. Cell 87:953–959.
58. Onate, S. A., S. Y. Tsai, M.-J. Tsai, and B. W. O'Malley. 1995. Sequence and characterization of a coactivator of the steroid hormone receptor superfamily. Science 270:1354–1357.
59. Orphanides, G., T. Lagrange, and D. Reinberg. 1996. The general transcription factors of RNA polymerase II. Genes Dev. 10:2657–2683.

60. Puigserver, P., Z. Wu, C. W. Park, R. Graves, M. Wright, and B. M. Spiegelman. 1998. A cold-inducible coactivator of nuclear receptors linked to adaptive thermogenesis. Cell 92:829–839.
61. Qi, J.-S., V. Desai-Yajnik, M. E. Greene, B. M. Raaka, and H. H. Samuels. 1995. The ligand binding domains of the thyroid hormone/retinoid receptor gene subfamily function in vivo to mediate heterodimerization, gene silencing, and transactivation. Mol. Cell. Biol. 15:1817–1825.
62. Rachez, C., Z. Suldan, J. Ward, C. P. Chang, D. Burakov, H. Erdjument-Bromage, P. Tempst, and L. P. Freedman. 1998. A novel protein complex that interacts with the vitamin D3 receptor in a ligand-dependent manner and enhances VDR transactivation in a cell-free system. Genes Dev. 12:1787–1800.
63. Renaud, J.-P., N. Rochel, M. Ruff, V. Vivat, P. Chambon, H. Gronemeyer, and D. Moras. 1995. Crystal structure of the RAR-γ ligand-binding domain bound to all-trans retinoic acid. Nature 378:681–689.
64. Schapira, M., M. Totrov, and R. A. Abagyan. 1999. Prediction of the binding energy for small molecules, peptides and proteins. J. Mol. Recognit. 12:1n press.
65. Schule, R., K. Umesono, D. J. Mangelsdorf, J. Bolado, J. W. Pike, and R. M. Evans. 1990. Jun-Fos and receptors for vitamins A and D recognize a common response element in the human osteocalcin gene. Cell 61:497–504.
66. Selmi-Ruby, S., J. Casanova, S. Malhotra, B. Roussett, B. M. Raaka, and H. H. Samuels. 1998. Role of the conserved C-terminal region of thyroid hormone receptor-α in ligand-dependent transcriptional activation. Mol. Cell. Endo. 138:105–114.
67. Shattil, S. J., T. O'Toole, M. Eigenthaler, V. Thon, M. Williams, B. M. Babior, and M. H. Ginsberg. 1995. β3-endonexin, a novel polypeptide that interacts specifically with the cytoplasmic tail of the integrin β3 subunit. J. Cell Biol. 131:807–816.
68. Sheikh, M. S., Z.-M. Shao, X.-S. Li, M. Dawson, A. M. Jetten, S. Wu, B. A. Conley, M. Garcia, H. Rochefort, and J. A. Fontana. 1994. Retinoid-resistant estrogen receptor-negative human breast carcinoma cells transfected with retinoic acid receptor-α acquire sensitivity to growth inhibition by retinoids. J. Biol. Chem. 269:21440–21447.
69. Spencer, T. E., G. Jenster, M. M. Burcin, C. D. Allis, J. Zhou, C. A. Mizzen, N. J. McKenna, S. A. Onate, S. Y. Tsai, M. J. Tsai, and B. W. O'Malley. 1997. Steroid receptor coactivator-1 is a histone acetyltransferase. Nature 389:194–198.
70. Strait, K., H. L. Schwartz, A. Perez-Castillo, and J. H. Oppenheimer. 1990. Relationship of c-erbA mRNA content to tissue triiodothyronine nuclear binding capacity and function in developing and adult rats. J. Biol. Chem. 265:10514–10521.
71. Strynadka, N. C., M. Eisenstein, E. Katchalski-Katzir, B. K. Shoichet, I. D. Kuntz, R. Abagyan, M. Totrov, J. Janin, J. Cherfils, F. Zimmerman, A. Olson, B. Duncan, M. Rao, R. Jackson, M. Sternberg, and M. N. James. 1996. Molecular docking programs successfully predict the binding of a beta-lactamase inhibitory protein to TEM-1 beta-lactamase. Nat. Struct. Biol. 3:233–239.
72. Sugawara, A., N. Sanno, N. Takahashi, R. Y. Osamura, and K. Abe. 1997. Retinoid X receptors in the kidney: their protein expression and functional significance. Endocrinology 138:3175–3180.
73. Takeshita, A., G. R. Cardona, N. Koibuchi, C. S. Suen, and W. W. Chin. 1997. TRAM-1, A novel 160-kDa thyroid hormone receptor activator molecule, exhibits distinct properties from steroid receptor coactivator-1. J. Biol. Chem. 272:27629–27634.
74. Torchia, J., D. W. Rose, J. Inostroza, Y. Kamei, S. Westin, C. K. Glass, and M. G. Rosenfeld. 1997. The transcriptional co-activator p/CIP binds CBP and mediates nuclear-receptor function. Nature 387:677–684.
75. Totrov, M., and R. Abagyan. 1994. Detailed ab initio prediction of lysozyme-antibody complex with 1.6 A accuracy. Nat. Struct. Biol. 1:259–263.
76. Totrov, M., and R. Abagyan. 1997. Flexible protein-ligand docking by global energy optimization in internal coordinates. Proteins Suppl 1:215–220.
77. Umesono, K., and R. M. Evans. 1989. Determinants of target gene specificity for steroid/thyroid hormone receptors. Cell 57:1139–1146.
78. Umesono, K., K. K. Murakami, C. C. Thompson, and R. M. Evans. 1991. Direct repeats as selective response elements for the thyroid hormone, retinoic acid, and vitamin D receptors. Cell 65:1255–1266.
79. Voegel, J. J., M. J. S. Heine, C. Zechel, P. Chambon, and H. Gronemeyer. 1996. TIF2, a 160 kDa transcriptional mediator for the ligand-dependent activation function AF-2 of nuclear receptors. EMBO J. 15:3667–3675.
80. Wagner, R. L., J. W. Apriletti, M. E. McGrath, B. L. West, J. D. Baxter, and R. J. Fletterick. 1995. A structural role for hormone in the thyroid hormone receptor. Nature 378:690–697.
81. Waterman, M. L., S. Adler, C. Nelson, G. L. Greene, R. M. Evans, and M. G. Rosenfeld. 1988. A single domain of the estrogen receptor confers deoxyribonucleic acid binding and transcriptional activation of the rat prolactin gene. Mol. Endocrinol. 2:14–21.
82. Willert, K., and R. Nusse. 1998. Beta-catenin: a key mediator of Wnt signaling. Curr Opin Genet Dev 8:95–102.
83. Yang, X. J., V. V. Ogryzko, J. Nishikawa, B. H. Howard, and Y. Nakatani. 1996. A p300/CBP-associated factor that competes with the adenoviral oncoprotein E1A. Nature 382:319–324.
84. Yao, T. P., G. Ku, N. Zhou, R. Scully, and D. M. Livingston. 1996. The nuclear hormone receptor coactivator SRC-1 is a specific target of p300. Proc. Nati. Acad. Sci. USA 93:10626–10631.
85. Yeh, S., and C. Chang. 1996. Cloning and characterization of a specific coactivator, ARA70, for the androgen receptor in human prostate cells. Proc. Natl. Acad. Sci. USA 93:5517–5521.
86. Yuan, C. X., M. Ito, J. D. Fondell, Z. Y. Fu, and R. G. Roeder. 1998. The TRAP220 component of a thyroid hormone receptor-associated protein (TRAP) coactivator complex interacts directly with nuclear receptors in a ligand-dependent fashion. Proc. Natl. Acad. Sci. USA 95:7939–7944.
87. Zhang, J. J., U. Vinkemeier, W. Gu, D. Chakravarti, C. M. Horvath, and J. E. D. Jr. 1996. Two contact regions between Stat1 and CBP/p300 in interferon gamma signaling. Proc. Natl. Acad. Sci. USA 93:15092–15096.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Patents, patent applications, and publications are cited throughout this application, the disclosures of which are incorporated herein by reference in their entireties.

What is claimed is:

1. An isolated nucleic acid molecule comprising a nucteotide sequence consisting of SEQ ID NO. 3 wherein the sequence encodes a functional NRIF3 nuclear hormone receptor co-activator polypeptide, wherein the NRIF3 binds in a ligand dependent manner to thyroid hormone receptor (TR) and retinoid X receptor (RXR), but does not interact with retinoic acid receptor (RAR), vitamin D receptor (VDR), progesterone receptor (PR), glucocorticoid receptor (GR), and estrogen receptor (ER) in a yeast two hybrid assay system or in vitro, or both, which polypeptide contains an LxxIL (SEQ ID NO:2) module in its C-terminal domain.

2. An isolated nucleic acid comprising a sequence that encodes an amino acid sequence consisting of SEQ ID NO:4 (FIG. 2).

3. An isolated nucleic acid sequence comprising a nucleotide sequence consisting of SEQ ID NO:3 (FIG. 2).

4. A vector comprising the nucleic acid sequence according to claim 3, wherein said nucleic acid sequence is operatively associated with an expression control sequence.

5. The vector according to claim 4 which is a plasmid.

6. A cell transfected with the vector according to claim 4.

7. The cell according to claim 6 which is a eukayotic cell.

8. The cell according to claim 7 which is a yeast cell.

9. A method for producing NRIF3 comprising culturing the cell according to claim 6 under conditions that permit expression of NRIF3.

* * * * *

SEQUENCE LISTING

<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<221> NAME/KEY: UNSURE
<222> LOCATION: (2)...(3)
<223> OTHER INFORMATION: Conserved motif for SRC-1 amd CBP/p300 with
      nuclear receptors;
      Xaa represents any amino acid

<400> SEQUENCE: 1

Leu Xaa Xaa Leu Leu
 1               5

<210> SEQ ID NO 2
<211> LENGTH: 5
<212> TYPE: PRT
<213> ORGANISM: Artificial Sequence
<220> FEATURE:
<221> NAME/KEY: UNSURE
<222> LOCATION: (2)...(3)
<223> OTHER INFORMATION: Domain of NRIF3 that interacts with liganded
      receptors;
      Xaa represents any amino acid

<400> SEQUENCE: 2

Leu Xaa Xaa Ile Leu
 1               5

<210> SEQ ID NO 3
<211> LENGTH: 592
<212> TYPE: DNA
<213> ORGANISM: Homo Sapien

<400> SEQUENCE: 3
cagcggcagt ggtgctttcc cgaatctcag aatgcctgtt aaaagatcac tgaagttgga      60
tggtctgtta gaagaaaatt catttgatcc ttcaaaaatc aaggaagaaa gtgttataac     120
ttattctcca acaactggaa cttgtcaaat gagtctattt gcttctccca caagttctga     180
agagcaaaag cacagaaatg gactatcaaa tgaaagagaa aaaaattga atcacccagt      240 ttaactgaaa gcaaagaatc tacaacaaaa gacaatgatg aattcatgat gttgctatca     300
aaagttgaga aattgtcaga gaaatcatg gagataatgc aaaatttaag tagtatacag      360
gctttggagg gcagtagaga gcttgaaaat ctcattggaa tctcctgtgc atcacatttc     420
taaaaagaga aatgcagaaa accaaagaac taatgacaaa gtgaataaac aaaactgttt     480
gaaaagagta caggacttcc tcacaaagca tcacgtcatc ttgacagcta tgaattcctt     540
aaagcatttt aaactgaggc attaagaaga aatgcactca ccatgagcac ca             592

<210> SEQ ID NO 4
<211> LENGTH: 177
<212> TYPE: PRT
<213> ORGANISM: Homo Sapien

<400> SEQUENCE: 4

Met Pro Val Lys Arg Ser Leu Lys Leu Asp Gly Leu Leu Glu Glu Asn
 1               5                  10                  15

Ser Phe Asp Pro Ser Lys Ile Thr Arg Lys Lys Ser Val Ile Thr Tyr
                20                  25                  30

-continued

```
Ser Pro Thr Thr Gly Thr Cys Gln Met Ser Leu Phe Ala Ser Pro Thr
            35                  40                  45

Ser Ser Glu Glu Gln Lys His Arg Asn Gly Leu Ser Asn Glu Lys Arg
 50                  55                  60

Lys Leu Asn His Pro Ser Leu Thr Glu Ser Lys Glu Ser Thr Thr
65                  70                  75                  80

Lys Asp Asn Asp Glu Phe Met Met Leu Leu Ser Lys Val Glu Lys Leu
                 85                  90                  95

Ser Glu Glu Ile Met Glu Ile Met Gln Asn Leu Ser Ser Ile Gln Ala
            100                 105                 110

Leu Glu Gly Ser Arg Glu Leu Glu Asn Leu Ile Gly Ile Ser Cys Ala
            115                 120                 125

Ser His Phe Leu Lys Arg Glu Met Gln Lys Thr Lys Glu Leu Met Thr
130                 135                 140

Lys Val Asn Lys Gln Lys Leu Phe Glu Lys Ser Thr Gly Leu Pro His
145                 150                 155                 160

Lys Ala Ser Arg His Leu Asp Ser Tyr Glu Phe Leu Lys Ala Ile Leu
                165                 170                 175

Asn
```

```
<210> SEQ ID NO 5
<211> LENGTH: 4
<212> TYPE: PRT
<213> ORGANISM: Artificial Sequence
<220> FEATURE:
<223> OTHER INFORMATION: Nuclear localization sequence of NRIF3

<400> SEQUENCE: 5

Lys Arg Lys Lys
 1
```

```
<210> SEQ ID NO 6
<211> LENGTH: 9
<212> TYPE: PRT
<213> ORGANISM: Artificial Sequence
<220> FEATURE:
<223> OTHER INFORMATION: C-terminus of beta3-endotoxin long form protein

<400> SEQUENCE: 6

Gly Gln Pro Gln Met Ser Pro Gln Leu
 1               5
```

```
<210> SEQ ID NO 7
<211> LENGTH: 17
<212> TYPE: PRT
<213> ORGANISM: Artificial Sequence
<220> FEATURE:
<223> OTHER INFORMATION: C-terminal peptide of NRIF3

<400> SEQUENCE: 7

Lys Ala Ser Arg His Leu Asp Ser Tyr Glu Phe Leu Lys Ala Ile Leu
 1               5                  10                  15

Asn
```

```
<210> SEQ ID NO 8
<211> LENGTH: 20
<212> TYPE: PRT
<213> ORGANISM: Artificial Sequence
<220> FEATURE:
<223> OTHER INFORMATION: 20-residue peptide of the second LxxLL box of
      SRC-1
```

```
<400> SEQUENCE: 8

Ser Leu Thr Glu Arg His Lys Ile Leu His Arg Leu Leu Gln Glu Gly
 1               5                  10                  15

Ser Pro Ser Asp
            20

<210> SEQ ID NO 9
<211> LENGTH: 12
<212> TYPE: DNA
<213> ORGANISM: Artificial Sequence
<220> FEATURE:
<223> OTHER INFORMATION: Idealized inverted repeat

<400> SEQUENCE: 9
aggtcatgac ct                                                               12

<210> SEQ ID NO 10
<211> LENGTH: 13
<212> TYPE: DNA
<213> ORGANISM: Artificial Sequence
<220> FEATURE:
<221> NAME/KEY: misc_feature
<222> LOCATION: (7)
<223> OTHER INFORMATION: DR1 sequence; n represent any nucleotide

<400> SEQUENCE: 10
aggtcanagg tca                                                              13
```